US009824188B2

(12) United States Patent
Brown et al.

(10) Patent No.: US 9,824,188 B2
(45) Date of Patent: *Nov. 21, 2017

(54) CONVERSATIONAL VIRTUAL HEALTHCARE ASSISTANT

(71) Applicant: Next IT Corporation, Spokane, WA (US)

(72) Inventors: Fred A Brown, Colbert, WA (US); Mitchell G. Lawrence, Liberty Lake, WA (US); Victor O'Brien Morrison, Colleyville, TX (US)

(73) Assignee: Next IT Corporation, Spokane Valley, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/446,153

(22) Filed: Jul. 29, 2014

(65) Prior Publication Data
US 2014/0337048 A1 Nov. 13, 2014

Related U.S. Application Data

(63) Continuation of application No. 13/607,414, filed on Sep. 7, 2012, now Pat. No. 9,536,049.

(51) Int. Cl.
*G06Q 50/22* (2012.01)
*G06Q 50/24* (2012.01)
(Continued)

(52) U.S. Cl.
CPC ...... *G06F 19/3418* (2013.01); *G06F 3/04886* (2013.01); *G06F 3/167* (2013.01);
(Continued)

(58) Field of Classification Search
CPC ..... G10L 15/22; G10L 15/26; G10L 15/1815; G10L 21/06; G10L 15/30; G10L 15/01;
(Continued)

(56) References Cited

U.S. PATENT DOCUMENTS 5,278,980 A 1/1994 Pedersen et al.
5,339,391 A 8/1994 Wroblewski et al.
(Continued)

FOREIGN PATENT DOCUMENTS

CN 103051669 4/2013
WO WO2011088053 7/2011

OTHER PUBLICATIONS

Office Action for U.S. Appl. No. 13/449,927, mailed on Aug. 15, 2014, Fred A. Brown, "Conversation User Interface", 29 pages.
(Continued)

*Primary Examiner* — Maroun Kanaan
(74) *Attorney, Agent, or Firm* — Lee & Hayes, PLLC

(57) ABSTRACT

A conversation user interface enables patients to better understand their healthcare by integrating diagnosis, treatment, medication management, and payment, through a system that uses a virtual assistant to engage in conversation with the patient. The conversation user interface conveys a visual representation of a conversation between the virtual assistant and the patient. An identity of the patient, including preferences and medical records, is maintained throughout all interactions so that each aspect of this integrated system has access to the same information. The conversation user interface presents allows the patient to interact with the virtual assistant using natural language commands to receive information and complete task related to his or her healthcare.

25 Claims, 12 Drawing Sheets

(51) Int. Cl.
*G06F 19/00* (2011.01)
*G10L 15/08* (2006.01)
*G10L 15/22* (2006.01)
*G06F 3/0488* (2013.01)
*G06F 3/16* (2006.01)

(52) U.S. Cl.
CPC .......... *G06F 19/322* (2013.01); *G06F 19/345* (2013.01); *G10L 15/08* (2013.01); *G10L 15/22* (2013.01); *G06F 19/326* (2013.01); *G06F 19/328* (2013.01); *G06F 19/3437* (2013.01); *G06F 19/3475* (2013.01); *G06F 19/3481* (2013.01)

(58) Field of Classification Search
CPC ... G10L 15/08; G10L 15/1822; G10L 15/183; G06Q 50/24; G06Q 50/22; G06Q 10/10; G06Q 50/20; G06F 19/321; G06F 19/3437; G06F 19/327; G06F 19/345; G06F 19/3481; G06F 17/30654; G06K 9/00201; G06K 2209/053; G06K 9/00
USPC ........................................................ 705/2, 3
See application file for complete search history.

(56) References Cited

U.S. PATENT DOCUMENTS

| | | |
|---|---|---|
| 5,418,948 A | 5/1995 | Turtle |
| 5,535,120 A | 7/1996 | Chong et al. |
| 5,615,112 A | 3/1997 | Liu Sheng et al. |
| 5,677,835 A | 10/1997 | Carbonell et al. |
| 5,682,539 A | 10/1997 | Conrad et al. |
| 5,727,174 A | 3/1998 | Aparicio, IV et al. |
| 6,012,053 A | 1/2000 | Pant et al. |
| 6,112,177 A | 8/2000 | Cosatto et al. |
| 6,144,938 A | 11/2000 | Surace et al. |
| 6,175,829 B1 | 1/2001 | Li et al. |
| 6,282,507 B1 | 8/2001 | Horiguchi et al. |
| 6,285,978 B1 | 9/2001 | Bernth et al. |
| 6,353,817 B1 | 3/2002 | Jacobs et al. |
| 6,388,665 B1 | 5/2002 | Linnett et al. |
| 6,396,951 B1 | 5/2002 | Grefenstette |
| 6,401,061 B1 | 6/2002 | Zieman |
| 6,658,627 B1 | 12/2003 | Gallup et al. |
| 6,661,418 B1 | 12/2003 | McMillan et al. |
| 6,757,362 B1 | 6/2004 | Cooper et al. |
| 6,826,540 B1 | 11/2004 | Plantec et al. |
| 6,829,603 B1 | 12/2004 | Chai et al. |
| 6,834,120 B1 | 12/2004 | LeClerc et al. |
| 6,987,514 B1 | 1/2006 | Beresin et al. |
| 6,999,932 B1 | 2/2006 | Zhou |
| 7,058,902 B2 | 6/2006 | Iwema et al. |
| 7,076,430 B1 | 7/2006 | Cosatto et al. |
| 7,194,483 B1 | 3/2007 | Mohan et al. |
| 7,263,493 B1 | 8/2007 | Provost et al. |
| 7,337,158 B2 | 2/2008 | Fratkina et al. |
| 7,426,697 B2 | 9/2008 | Holecek et al. |
| 7,483,829 B2 | 1/2009 | Murakami et al. |
| 7,536,413 B1 | 5/2009 | Mohan et al. |
| 7,539,656 B2 | 5/2009 | Fratkina et al. |
| 7,548,899 B1 | 6/2009 | Del Favero, Jr. et al. |
| 7,558,792 B2 | 7/2009 | Bier |
| 7,599,831 B2 | 10/2009 | Ford |
| 7,610,382 B1 | 10/2009 | Siegel |
| 7,711,547 B2 | 5/2010 | Abir |
| 7,739,604 B1 | 6/2010 | Lyons |
| 7,797,146 B2 | 9/2010 | Harless et al. |
| 7,818,183 B2 * | 10/2010 | Schoenberg .......... G06F 19/327 705/2 |
| 7,912,701 B1 | 3/2011 | Gray et al. |
| 7,970,663 B2 | 6/2011 | Ganz et al. |
| 8,160,979 B1 | 4/2012 | Evans et al. |
| 8,346,563 B1 | 1/2013 | Hjelm et al. |
| 8,352,266 B2 | 1/2013 | Farmaner et al. |
| 8,401,842 B1 | 3/2013 | Ginzburg et al. |
| 8,433,556 B2 | 4/2013 | Fraser et al. |
| 8,473,420 B2 | 6/2013 | Bohus et al. |
| 8,510,276 B2 | 8/2013 | Haiby et al. |
| 8,519,963 B2 | 8/2013 | Kocienda |
| 8,670,979 B2 | 3/2014 | Gruber et al. |
| 8,677,377 B2 | 3/2014 | Cheyer et al. |
| 8,731,929 B2 | 5/2014 | Kennewick et al. |
| 8,756,326 B1 | 6/2014 | Elberse et al. |
| 8,762,152 B2 | 6/2014 | Bennett et al. |
| 8,930,191 B2 | 1/2015 | Gruber et al. |
| 8,942,986 B2 | 1/2015 | Cheyer et al. |
| 8,943,094 B2 | 1/2015 | Brown et al. |
| 9,117,447 B2 | 8/2015 | Gruber et al. |
| 9,202,171 B2 | 12/2015 | Kuhn |
| 9,501,741 B2 | 11/2016 | Cheyer et al. |
| 2001/0000356 A1 | 4/2001 | Woods |
| 2001/0033298 A1 | 10/2001 | Slotznick |
| 2001/0044751 A1 | 11/2001 | Pugliese, III et al. |
| 2001/0049688 A1 | 12/2001 | Fratkina et al. |
| 2001/0053968 A1 | 12/2001 | Galitsky et al. |
| 2002/0008716 A1 | 1/2002 | Colburn et al. |
| 2002/0032591 A1 | 3/2002 | Mahaffy et al. |
| 2002/0123994 A1 | 9/2002 | Schabes et al. |
| 2002/0129031 A1 | 9/2002 | Lau et al. |
| 2003/0004908 A1 | 1/2003 | Linthicum et al. |
| 2003/0041307 A1 | 2/2003 | Park |
| 2003/0061029 A1 | 3/2003 | Shaket |
| 2003/0088547 A1 | 5/2003 | Hammond |
| 2003/0126089 A1 | 7/2003 | Fukuoka et al. |
| 2003/0126090 A1 | 7/2003 | Fukuoka et al. |
| 2003/0142829 A1 | 7/2003 | Avigni |
| 2003/0212544 A1 | 11/2003 | Acero et al. |
| 2004/0107088 A1 | 6/2004 | Budzinski |
| 2004/0141013 A1 | 7/2004 | Alcazar et al. |
| 2004/0186705 A1 | 9/2004 | Morgan et al. |
| 2005/0027694 A1 | 2/2005 | Sauermann |
| 2005/0054381 A1 | 3/2005 | Lee et al. |
| 2005/0120276 A1 | 6/2005 | Kolawa et al. |
| 2006/0004826 A1 | 1/2006 | Zartler et al. |
| 2006/0020466 A1 | 1/2006 | Cousineau et al. |
| 2006/0036430 A1 | 2/2006 | Hu |
| 2006/0037076 A1 | 2/2006 | Roy |
| 2006/0047632 A1 | 3/2006 | Zhang |
| 2006/0067352 A1 | 3/2006 | John et al. |
| 2006/0074689 A1 | 4/2006 | Cosatto et al. |
| 2006/0080107 A1 | 4/2006 | Hill et al. |
| 2006/0092978 A1 | 5/2006 | John et al. |
| 2006/0161414 A1 | 7/2006 | Carignano et al. |
| 2006/0253427 A1 | 11/2006 | Wu et al. |
| 2007/0043687 A1 | 2/2007 | Bodart et al. |
| 2007/0100790 A1 | 5/2007 | Cheyer et al. |
| 2007/0106670 A1 | 5/2007 | Yoakum et al. |
| 2007/0130112 A1 | 6/2007 | Lin |
| 2007/0134631 A1 | 6/2007 | Hardy et al. |
| 2007/0156677 A1 | 7/2007 | Szabo |
| 2007/0185702 A1 | 8/2007 | Harney et al. |
| 2007/0197296 A1 | 8/2007 | Lee |
| 2007/0242656 A1 | 10/2007 | Klassen et al. |
| 2007/0265533 A1 * | 11/2007 | Tran .......... A61B 5/021 600/481 |
| 2007/0294229 A1 | 12/2007 | Au |
| 2008/0005158 A1 | 1/2008 | Zartler et al. |
| 2008/0010268 A1 | 1/2008 | Liao et al. |
| 2008/0016040 A1 | 1/2008 | Jones et al. |
| 2008/0036756 A1 | 2/2008 | Gaos et al. |
| 2008/0091406 A1 | 4/2008 | Baldwin et al. |
| 2008/0133444 A1 | 6/2008 | Gao et al. |
| 2008/0162498 A1 | 7/2008 | Omoigui |
| 2008/0222734 A1 | 9/2008 | Redlich et al. |
| 2008/0235604 A1 | 9/2008 | Ebert |
| 2008/0305815 A1 | 12/2008 | McDonough |
| 2009/0006525 A1 | 1/2009 | Moore |
| 2009/0030800 A1 | 1/2009 | Grois |
| 2009/0063427 A1 | 3/2009 | Zuta et al. |
| 2009/0070103 A1 | 3/2009 | Beggelman et al. |
| 2009/0077488 A1 | 3/2009 | Ording |
| 2009/0089100 A1 * | 4/2009 | Nenov .......... G06F 19/322 705/3 |

(56) References Cited

U.S. PATENT DOCUMENTS

| | | |
|---|---|---|
| 2009/0119095 A1 | 5/2009 | Beggelman et al. |
| 2009/0119587 A1 | 5/2009 | Allen et al. |
| 2009/0157386 A1 | 6/2009 | Zhou |
| 2009/0171923 A1 | 7/2009 | Nash et al. |
| 2009/0182702 A1 | 7/2009 | Miller |
| 2009/0204677 A1 | 8/2009 | Michaelis et al. |
| 2009/0216691 A1 | 8/2009 | Borzestowski et al. |
| 2009/0225041 A1 | 9/2009 | Kida et al. |
| 2009/0227223 A1 | 9/2009 | Jenkins |
| 2009/0228264 A1 | 9/2009 | Williams et al. |
| 2009/0235356 A1 | 9/2009 | Jensen et al. |
| 2009/0248399 A1 | 10/2009 | Au |
| 2009/0271205 A1 | 10/2009 | Finn et al. |
| 2010/0005122 A1 | 1/2010 | Jackson |
| 2010/0030549 A1 | 2/2010 | Lee et al. |
| 2010/0050237 A1 | 2/2010 | Bokor et al. |
| 2010/0070448 A1 | 3/2010 | Omoigui |
| 2010/0070871 A1 | 3/2010 | Liesche et al. |
| 2010/0153398 A1 | 6/2010 | Miller et al. |
| 2010/0169336 A1 | 7/2010 | Eckhoff-Hornback et al. |
| 2010/0218113 A1 | 8/2010 | White et al. |
| 2010/0226490 A1 | 9/2010 | Schultz et al. |
| 2010/0235808 A1 | 9/2010 | Dayan et al. |
| 2010/0281012 A1 | 11/2010 | Imig et al. |
| 2010/0312547 A1 | 12/2010 | Van Os et al. |
| 2011/0071819 A1 | 3/2011 | Miller et al. |
| 2011/0078105 A1 | 3/2011 | Wallace |
| 2011/0119196 A1 | 5/2011 | Ventura et al. |
| 2011/0179126 A1 | 7/2011 | Wetherell et al. |
| 2011/0213642 A1 | 9/2011 | Makar et al. |
| 2011/0282664 A1 | 11/2011 | Tanioka et al. |
| 2011/0288947 A1 | 11/2011 | Biran |
| 2011/0301982 A1 | 12/2011 | Green, Jr. et al. |
| 2011/0307245 A1 | 12/2011 | Hanneman et al. |
| 2012/0016678 A1 | 1/2012 | Gruber et al. |
| 2012/0022872 A1 | 1/2012 | Gruber et al. |
| 2012/0030553 A1 | 2/2012 | Delpha et al. |
| 2012/0041903 A1 | 2/2012 | Beilby et al. |
| 2012/0078891 A1 | 3/2012 | Brown et al. |
| 2012/0110473 A1 | 5/2012 | Tseng |
| 2012/0117005 A1 | 5/2012 | Spivack |
| 2012/0221502 A1 | 8/2012 | Jerram et al. |
| 2012/0245926 A1* | 9/2012 | Montyne ............... G10L 15/26 704/9 |
| 2012/0253825 A1 | 10/2012 | Di Fabbrizio et al. |
| 2012/0265528 A1 | 10/2012 | Gruber et al. |
| 2012/0284040 A1 | 11/2012 | Dupin |
| 2012/0311541 A1 | 12/2012 | Bullard et al. |
| 2013/0017523 A1 | 1/2013 | Barborak et al. |
| 2013/0031476 A1 | 1/2013 | Coin et al. |
| 2013/0046149 A1 | 2/2013 | Gettelman et al. |
| 2013/0152092 A1 | 6/2013 | Yadgar |
| 2013/0204813 A1 | 8/2013 | Master et al. |
| 2013/0254139 A1 | 9/2013 | Lei |
| 2013/0258040 A1 | 10/2013 | Kaytaz et al. |
| 2013/0262467 A1 | 10/2013 | Zhang et al. |
| 2013/0275875 A1 | 10/2013 | Gruber et al. |
| 2013/0283168 A1 | 10/2013 | Brown et al. |
| 2014/0029734 A1 | 1/2014 | Kim et al. |
| 2014/0040748 A1 | 2/2014 | Lemay et al. |
| 2014/0047001 A1 | 2/2014 | Phillips et al. |
| 2014/0053102 A1 | 2/2014 | Lee et al. |
| 2014/0074454 A1 | 3/2014 | Brown et al. |
| 2014/0115456 A1 | 4/2014 | White et al. |
| 2014/0164476 A1 | 6/2014 | Thomson |
| 2014/0164508 A1 | 6/2014 | Lynch et al. |
| 2014/0181741 A1 | 6/2014 | Apacible et al. |
| 2014/0201675 A1 | 7/2014 | Joo et al. |
| 2014/0244266 A1 | 8/2014 | Brown et al. |
| 2014/0244712 A1 | 8/2014 | Walters et al. |
| 2014/0245140 A1 | 8/2014 | Brown et al. |
| 2014/0282109 A1 | 9/2014 | Wenger et al. |
| 2014/0297284 A1 | 10/2014 | Gruber et al. |
| 2014/0310005 A1 | 10/2014 | Brown et al. |
| 2014/0317502 A1 | 10/2014 | Brown et al. |
| 2014/0343924 A1 | 11/2014 | Brown et al. |
| 2014/0343928 A1 | 11/2014 | Brown et al. |
| 2014/0365223 A1 | 12/2014 | Brown et al. |
| 2014/0365407 A1 | 12/2014 | Brown et al. |
| 2015/0066817 A1 | 3/2015 | Slayton et al. |
| 2015/0185996 A1 | 7/2015 | Brown et al. |
| 2015/0186154 A1 | 7/2015 | Brown et al. |
| 2015/0186155 A1 | 7/2015 | Brown et al. |
| 2015/0186156 A1 | 7/2015 | Brown et al. |
| 2015/0363697 A1 | 12/2015 | Spivack |
| 2016/0012186 A1 | 1/2016 | Zasowski et al. |
| 2016/0110071 A1 | 4/2016 | Brown et al. |
| 2017/0132220 A1 | 5/2017 | Brown et al. |

OTHER PUBLICATIONS

Final Office Action for U.S. Appl. No. 13/449,927, mailed on Apr. 9, 2015, Fred A. Brown, "Conversation User Interface", 35 pages.

Office Action for U.S. Appl. No. 13/607,414, mailed on Jul. 21, 2015, Fred A. Brown, "Conversational Virtual Healthcare Assistant", 25 pages.

U.S. Appl. No. 13/774,381, filed Feb. 22, 2013, Fred A. Brown et al., "Interaction with a Portion of a Content Item through a Virtual Assistant," 68 pages.

U.S. Appl. No. 13/774,519, filed Feb. 22, 2013, Fred A. Brown et al, "Virtual Assistant Transfer between Smart Devices," 65 pages.

"5 wearable electronic phones", retrieved on Feb. 13, 2015 at <<http://limcorp.net/2009/5-wearable-electronic-phones>>, 12 pages.

"AskJennMediaCoverage", retrieved on Nov. 12, 2014, 76 pages.

"Case Study With Alme, Alaska Airlines soars", retrieved on Apr. 10, 2015 at <<http://www.nextit.com/media/downloads/Case-study-Alaska-Air.pdf>>, 3 pages.

Cassell, et al., "Embodied Conversational Agents", MIT Press, 2000, pp. 272 and 275.

Final Office Action for U.S. Appl. No. 12/014,229, mailed on Nov. 25, 2013, Tanya M. Miller, "Active Lab", 15 pages.

Final Office Action for U.S. Appl. No. 12/636,571, mailed on Nov. 7, 2013, Tanya Miller, "Leveraging Concepts With Information Retrieval Techniques and Knowledge Bases", 31 pages.

"Frost & Sullivan Commends Next IT for Leading the Virtual Agent Applications Industry in Competitive Strategy Innovation", Frost & Sullivan, Dec. 18, 2014, 5 pages.

"Meet Jenn, Your Virtual Assistant at alaskaair.com", retrieved on Apr. 13, 2015 at <<http://www.alaskaair.com/content/about-us/site-info/ask-jenn.aspx>>, 1 page.

Office action for U.S. Appl. No. 14/293,673, mailed on Jan. 15, 2016, Brown et al., "Virtual Assistant Conversations", 29 pages.

Office action for U.S. Appl. No. 14/451,009, mailed on Jan. 5, 2016, Brown et al., "Wearable-Based Virtual Agents", 10 pages.

Office Action for U.S. Appl. No. 14/293,529, mailed on Oct. 1, 2015, Fred A. Brown, "Virtual Assistant Team Identification", 18 pages.

Office Action for U.S. Appl. No. 14/467,715, mailed on Oct. 1, 2014, Fred Brown, "Virtual Assistant Conversations", 14 pages.

Office action for U.S. Appl. No. 14/302,096, mailed on Oct. 8, 2014, Brown, "Active Lab", 27 pages.

Office Action for U.S. Appl. No. 13/341,261, mailed on Nov. 6, 2014, Fred A. Brown, "Providing Variable Responses in a Virtual-Assistant Environment", 26 pages.

Non-Final Office Action for U.S. Appl. No. 12/564,546, mailed on Dec. 21, 2011, Tanya Miller et al., "Apparatus, System, and Method for Natural Language Processing", 12 pages.

Final Office Action for U.S. Appl. No. 14/293,673, mailed on Dec. 4, 2014, Fred A. Brown, "Virtual Assistant Conversations", 22 pages.

Office Action for U.S. Appl. No. 14/315,852, mailed on Dec. 4, 2014, Fred Brown, "Virtual Assistant Conversations for Ambiguous User Input and Goals", 15 pages.

Office Action for U.S. Appl. No. 14/451,009, mailed on Dec. 4, 2014, Fred Brown, "Wearable-Based Virtual Agents", 9 pages.

Office Action for U.S. Appl. No. 12/014,229, mailed on Feb. 13, 2015, Tanya M. Miller, "Active Lab", 16 pages.

(56) References Cited

OTHER PUBLICATIONS

Office action for U.S. Appl. No. 14/293,586, mailed on Feb. 17, 2015, Brown et al., "Virtual Assistant Team Customization", 11 pages.
Office action for U.S. Appl. No. 14/467,221, mailed on Feb. 17, 2015, Brown et al., "Context-Based Virtual Assistant Conversations", 5 pages.
Office action for U.S. Appl. No. 14/467,221, mailed on Feb. 18, 2016, Brown et al., "Context-Based Virtual Assistant Conversations", 14 pages.
Final Office Action for U.S. Appl. No. 14/293,529, mailed on Feb. 23, 2015, Fred A. Brown, "Virtual Assistant Team Identification", 17 pages.
Final Office Action for U.S. Appl. No. 12/564,546, mailed on Feb. 26, 2013, Tanya Miller et al., "Apparatus, System, and Method for Natural Language Processing", 15 pages.
Office action for U.S. Appl. No. 14/293,619, mailed on Feb. 26, 2016, Brown et al., "Virtual Assistant Acquisitions and Training", 16 pages.
Final Office Action for U.S. Appl. No. 13/341,261, mailed on Feb. 27, 2014, Fred A. Brown, "Providing Variable Responses in a Virtual-Assistant Environment", 32 pages.
Non-Final Office Action for U.S. Appl. No. 12/014,229, mailed on Mar. 15, 2013, Tanya M. Miller, "Active Lab", 14 pages.
Office action for U.S. Appl. No. 14/293,529, mailed on Mar. 17, 2016, Brown et al., "Virtual Assistant Team Identification", 19 pages.
Office action for U.S. Appl. No. 14/293,586, mailed on Mar. 17, 2016, Brown et al., "Virtual Assistant Team Customization", 13 pages.
Office action for U.S. Appl. No. 12/636,571, mailed on Mar. 24, 2016, Miller et al., "Leveraging Concepts With Information Retrieval Techniques and Knowledge Bases", 31 pages.
Office action for U.S. Appl. No. 13/341,261, mailed on Mar. 24, 2016, Brown et al., "Providing Variable Responses in a Virtual-Assistant Environment", 30 pages.
Final Office Action for U.S. Appl. No. 14/315,852, mailed on Apr. 10, 2015, Fred Brown, "Virtual Assistant Conversations for Ambiguous User Input and Goals", 18 pages.
Non-Final Office Action for U.S. Appl. No. 12/636,571, mailed on Apr. 12, 2013, Tanya Miller et al., "Leveraging Concepts With Information Retrieval Techniques and Knowledge Bases", 31 pages.
Final Office Action for U.S. Appl. No. 14/293,619, mailed on Apr. 13, 2015, Fred A. Brown, "Virtual Assistant Acquisitions and Training", 17 pages.
Final Office Action for U.S. Appl. No. 14/467,715, mailed on Apr. 16, 2015, Fred Brown, "Virtual Assistant Conversations", 5 pages.
Office action for U.S. Appl. No. 14/467,715, mailed on May 18, 2016, Brown et al., "Virtual Assistant Conversations", 14 pages.
Office action for U.S. Appl. No. 13/341,261, mailed on May 21, 2015, Brown et al., "Providing Variable Responses in a Virtual-Assistant Environment", 30 pages.
Final Office Action for U.S. Appl. No. 14/451,009, mailed on May 21, 2015, Fred Brown, "Wearable-Based Virtual Agents", 10 pages.
Non-Final Office Action for U.S. Appl. No. 12/564,546, mailed on Jun. 12, 2013, Tanya Miller et al., "Apparatus, System, and Method for Natural Language Processing", 18 pages.
Final Office Action for U.S. Appl. No. 12/636,571, mailed on Jun. 12, 2015, Tanya Miller, "Leveraging Concepts With Information Retrieval Techniques and Knowledge Bases", 37 pages.
Final Office Action for U.S. Appl. No. 14/293,529, mailed on Jun. 15, 2015, Fred A. Brown, "Virtual Assistant Team Identification", 16 pages.
Final Office Action for U.S. Appl. No. 14/293,586, mailed on Jul. 24, 2015, Fred A. Brown, "Virtual Assistant Team Customization", 14 pages.
Office Action for U.S. Appl. No. 14/293,673, mailed on Jul. 24, 2015, Fred A. Brown, "Virtual Assistant Conversations", 25 pages.
Final Office Action for U.S. Appl. No. 14/302,096, mailed on Jul. 29, 2015, Fred Brown, "Active Lab", 7 pages.
Office Action for U.S. Appl. No. 14/293,619, mailed on Aug. 13, 2015, Fred A. Brown, "Virtual Assistant Acquisitions and Training", 17 pages.
Office action for U.S. Appl. No. 13/341,261, mailed on Aug. 14, 2013, Brown et al., "Providing Variable Responses in a Virtual-Assistant Environment", 22 pages.
Office action for U.S. Appl. No. 12/636,571, mailed on Aug. 14, 2014, Miller et al., "Leveraging Concepts With Information Retrieval Techniques and Knowledge Bases", 35 pages.
Office action for U.S. Appl. No. 14/293,529, mailed on Sep. 10, 2014, Brown et al., "Virtual Assistant Team Identification", 13 pages.
Office Action for U.S. Appl. No. 13/341,261, mailed on Sep. 23, 2015, Fred A. Brown, "Providing Variable Responses in a Virtual-Assistant Environment", 26 pages.
Office Action for U.S. Appl. No. 14/315,852, mailed on Sep. 24, 2015, Fred Brown, "Virtual Assistant Conversations for Ambiguous User Input and Goals", 6 pages.
Office action for U.S. Appl. No. 14/293,619, mailed on Sep. 8, 2014, Brown et al., "Virtual Assistant Acquisitions and Training", 15 pages.
Office action for U.S. Appl. No. 14/293,673, mailed on Sep. 8, 2014, Riegler et al., "Virtual Assistant Conversations", 22 pages.
Office Action for U.S. Appl. No. 14/302,096, mailed on Jan. 12, 2015, Fred Brown, "Active Lab", 4 pages.
Office action for U.S. Appl. No. 14/467,221, mailed on Oct. 9, 2014, Brown, "Context-Based Virtual Assistant Conversations", 24 pages.
Office action for U.S. Appl. No. 12/014,229, mailed on Nov. 19, 2015, Inventor #1, "Active Lab", 8 pages.
Pandorabots Inc., "AIML Targeting: Supervised Learning for Bots", uploaded on Oct. 29, 2009, at https:// www.youtube.com/watch?v=aGe30NTVDOk.
PCT Search Report and Written Opinion mailed Nov. 12, 2014 for PCT Application No. PCT/US14/31047, 14 Pages.
PCT Search Report and Written Opinion mailed Sep. 2, 2015 for PCT Application No. PCT/US15/33594, 9 pages.
"SGT STAR Wins Intelligent Assistant Award", San Francisco, Calif (PRWEB) Sep. 24, 2014, PRWEB Online Visibility from Vocus, 2 pages.
"TAM", Case Study Meet Juli—TAM Airlines' most famous new hire, Next IT Corporation, Apr. 6, 2015, 2 pages.
"The Army's Recruiter", New York Public Radio, Media File, Retrieved on Nov. 11, 2014, 9 minutes 1 second.
"The Armys Robot Recruiter", Transcript from New York Public Radio, Aug. 8, 2014, 3 pages.
"Undercover Virtual Agent Article", KOMO News, retrieved Nov. 12, 2014, 2 pages.
Office Action for U.S. Appl. No. 14/293,529, mailed on Jan. 31, 2017, Fred A. Brown, "Virtual Assistant Team Identification", 20 pages.
Office action for U.S. Appl. No. 12/636,571, mailed on Feb. 15, 2017, Miller et al., "Leveraging Concepts With Information Retrieval Techniques and Knowledge Bases", 35 pages.
Office Action for U.S. Appl. No. 13/341,261, mailed on Feb. 7, 2017, Fred A. Brown, "Providing Variable Responses in a Virtual-Assistant Environment", 34 pages.
AppleKeynotes, "Apple Special Event 2011—Siri Introduction", YouTube, retrieved on Oct. 21, 2016 at <<https://www.youtube.com/watch?v=agzItTz35QQ>>, Mar. 22, 2013, 1 page.
The Supplementary European Search Report dated Oct. 31, 2016 for European Patent Application No. 14785575.3, 10 pages.
Office action for U.S. Appl. No. 14/293,619, dated Oct. 6, 2016, Brown et al., "Virtual Assistant Acquisitions and Training", 17 pages.
Office action for U.S. Appl. No. 14/293,673, dated Nov. 1, 2016, Brown et al., "Virtual Assistant Conversations", 34 pages.
Office action for U.S. Appl. No. 12/014,229, dated Nov. 16, 2016, Miller, "Active Lab", 8 pages.
Office action for U.S. Appl. No. 14/467,221, dated Nov. 3, 2016, Brown et al., "Context-Based Virtual Assistant Conversations", 15 pages.
Office action for U.S. Appl. No. 13/865,789, dated Nov. 7, 2016, Brown et al., "Virtual Assistant Focused User Interfaces", 20 pages.

(56) References Cited

OTHER PUBLICATIONS

Office action for U.S. Appl. No. 14/293,529, dated Aug. 31, 2016, Brown et al., "Virtual Assistant Team Identification", 18 pages.
Office Action for U.S. Appl. No. 13/341,261, dated Sep. 15, 2016, Fred A. Brown, "Providing Variable Responses in a Virtual-Assistant Environment", 29 pages.
Office action for U.S. Appl. No. 14/293,586, dated Sep. 23, 2016, Brown et al., "Virtual Assistant Team Customization", 9 pages.
Office Action for U.S. Appl. No. 14/302,096, dated Sep. 27, 2016, Brown et al., "Regression Testing", 6 pages.
Office action for U.S. Appl. No. 14/467,715, dated Dec. 1, 2016, Brown et al., "Virtual Assistant Conversations", 10 pages.
Extended European Search Report dated Mar. 17, 2017 for European patent application No. 14785575.3, 16 pages.
Final Office Action for U.S. Appl. No. 14/293,673, dated Apr. 25, 2017, Fred A. Brown, "Virtual Assistant Conversations", 32 pages.
Office action for U.S. Appl. No. 13/865,789, dated May 19, 2017, Brown et al., "Virtual Assistant Focused User Interfaces", 22 pages.
Office action for U.S. Appl. No. 14/293,619, dated May 4, 20017, Brown et al., "Virtual Assistant Acquisitions and Training", 18 pages.
Office Action for U.S. Appl. No. 12/014,229, dated Jun. 08, 2017, Tanya M. Miller, "Active Lab", 10 pages.
Langkilde, Irene et al., "Automatic Prediction of Problematic Human-Computer Dialogues in 'How May I Help You?'", AT&T Labs Research, 1999, 5 pages.
Walker, Marilyn et al., "Learning to Predict Problematic Situations in a Spoken Dialogue System: Experiments with How May I Help You?", AT&T Labs Research, NAACL 2000 Proceedings of the 1st North American chapter of the Association for Computational Linguistics conference, Seattle, Washington, Apr. 29-May 4, 2000, 8 pages.
Office Action for U.S. Appl. No. 14/837,282, dated Jan. 20, 2017, Spivack, "System and Method for Providing Distributed Intelligent Assistance", 16 pages.
Office Action for U.S. Appl. No. 13/271,175, dated Oct. 7, 2014, Nova T. Spivack, "System and Method for Providing Distributed Intelligent Assistance", 14 pages.
Final Office Action for U.S. Appl. No. 13/271,175, dated May 30, 2014, Nova T. Spivack, "System and Method for Providing Distributed Intelligent Assistance", 14 pages.
Non-Final Office Action for U.S. Appl. No. 13/271,175, dated Jul. 19,2013, Nova T Spivack, "System and Method for Providing Distributed Intelligent Assistance ", 13 pages.
Office action for U.S. Appl. No. 14/467,221, dated Jul. 25, 2017, Brown et al., "Context-Based Virtual Assistant Conversations", 15 pages.
Office Action for U.S. Appl. No. 14/467,715, dated Jul. 25, 2017, Brown et al., "Virtual Assistant Conversations", 12 pages.
Office Action for U.S. Appl. No. 14/837,282, dated Oct. 20, 2015, Nova T. Spivack, "System and Method for Providing Distributed Intelligent Assistance", 8 pages.
Krahmer, Emiel et al., "Problem Spotting in Human-Machine Interaction", IPO, Center for Research on User-System Interaction, Sixth European Conference on Speech Communication and Technology, Sep. 5-9, 1999, Budapest, Hungary, 4 pages.

\* cited by examiner

CONVERSATIONAL VIRTUAL HEALTHCARE ASSISTANT

RELATED APPLICATIONS

This application claims priority to and is a continuation of U.S. patent application Ser. No. 13/607,414, filed on Sep. 7, 2012, the entire contents of which are incorporated herein by reference.

BACKGROUND

A large and growing population of users accesses information via websites or downloaded client applications provided by respective service providers. Accessing this information "online," rather than in person or over the phone, provides numerous benefits to both the service providers and the end users. For instance, the service providers are able to offer an array of information on their websites for access by end users at any time of day and without the cost associated with providing a human representative to help end users seek desired information. In many instances, this information may be of the type that a human representative of the service provider need not spend time relaying to customers, such as contact information of the service provider (e.g., physical location, phone number, etc.), hours in which the service provider is open, items (e.g., products, services, etc.) offered by the service provider, and the like.

While providing this type of information to end users in this manner is both convenient for users and saves costs for a service provider, the amount of available information can be overwhelming from both a management and an accessibility standpoint. For instance, a user may visit a website of a service provider to seek a particular piece of information or to make a particular request to the service provider. However, because of the massive amount of content and navigation paths offered by the website, the user may find that the desired information is akin to the proverbial needle in the haystack. As such, the user may get frustrated and cease working with the service provider or may call a human representative of the service provider for help, thus eliminating the cost savings associated with providing this information on the website.

To alleviate this problem, service providers may employ a "virtual assistant" to act as an interface between end users and the information on the service provider site. In some instances, this virtual assistant embodies a human representative of the service provider that is displayed on a website, client application, or the like of the service provider. The virtual assistant may also include an interface (e.g., a text box) that allows users to input queries, such as "where are you located?" or "when are you open?" in response to receiving such a query, the service provider or a third party utilizes natural language processing techniques to attempt to identify the contents of the user's query. After identifying these contents, the service provider or the third party identifies a response to provide to the user via the virtual assistant, such as "we are located at 555 N. $5^{th}$ Street" or "we are open from 9 am to 7 pm today."

Virtual assistants thus act as an effective interface that allows users to seek information they desire while still allowing service providers to realize cost savings associated with providing information online rather than via a human representative. While these virtual assistants are helpful to both end users and service providers, increasing the ability of these virtual assistants to emulate human representatives remains a priority.

Another trend concerns the expanding use of mobile devices, such as smart phones, portable digital assistants, and tablets, to offer a wide variety of functionality. Users are accustomed to using their mobile devices to make phone calls, send emails, surf the web, find entertainment or eating establishments, use as a GPS navigation unit in finding locations, and so on.

As users engage computing devices for an ever growing diversity of functions, there has been a growing need to improve the way users interact with the devices. Traditional techniques of keyboards and keypads are being replaced or supplemented by touch interfaces. Further, there is a growing desire to verbally interact with computing devices.

With these technology advances, however, user expectations increase. Being able to simply speak commands to a computing device was once impressive; today, this is commonplace and expected. Where users were once satisfied with one word commands or simple phrases, users are demanding better experiences with smarter devices that understand more.

Accordingly, there is a continuing need for better ways to facilitate user interaction with a computing device, particularly in the mobile space where keyboard-based input is limited and voice interaction is increasing in popularity.

Overlay this continuing need with the sophisticated subject matter of healthcare. A large population segment engages the healthcare system on a daily basis, from taking medicine, to visiting healthcare personnel, to exercise and diet programs. There can be an overwhelming amount of healthcare information that users are often expected to synthesize and implement. Doctors, nurses, and other healthcare professionals are becoming increasingly busy as the population ages and more seniors require more healthcare attention. Accordingly, this is a growing need to help patients understand the voluminous amounts of data and information about their health, particularly when healthcare professionals are not available on a daily basis.

SUMMARY

This document describes a conversational virtual assistant that aids patients in fulfilling their healthcare needs. As part of this assistance, a conversation graphical user interface (GUI) is employed by the virtual healthcare assistant that enables users to better understand their interactions with the assistant, particularly when speech input and output is involved.

The virtual healthcare assistant helps the patient manage all of the healthcare information, personal healthcare records, medication regimens, appointments, health insurance, and other aspects of healthcare. In one implementation, the virtual healthcare assistant employs a conversation GUI to convey a visual representation of a conversation between the virtual healthcare assistant and the user. The conversation GUI presents a series of dialog representations, such as dialog bubbles, which include user-originated dialog representations associated with input from a user (verbal, textual, or otherwise) and device-originated dialog representations associated with response from the device or virtual assistant. Associated with one or more of the dialog representations are one or more graphical elements to convey assumptions made to interpret the user input and derive an associated response. The conversation GUI enables the user to see the assumptions upon which the response was based, and to optionally change the assumption(s). Upon change of an assumption, the conversation GUI is refreshed to present a modified dialog representation of a new response derived from the altered set of assumptions. In this way, the user can intuitively understand why the computing device responded as it did. For instance, by revealing the assumptions, the user can quickly learn whether the device misunderstood the verbal input (i.e., potentially a speech recognition issue) or whether the device misinterpreted the verbal input (i.e., potentially a natural language processing issue).

This conversation GUI is leveraged to assist in any number of sophisticated and important healthcare dialogs. For instance, suppose the patient has diabetes and would like to administer insulin medication. The virtual healthcare assistant can wake up and tell the patient that it is time to take the medication. In reply, the patient may simply ask about dosage and location to administer the shot. The virtual healthcare assistance can then output a spoken reply with the dosage and location, together with depicting a picture of the body location and illustrating where and how to place the needle. This is but one example.

The virtual healthcare assistant may help with essentially any healthcare task, including maintaining lab values, electronic health records, and patient health records; submitting insurance claims and understanding insurance coverage eligibility; presenting clinical guidelines, research, and medical information; explaining sophisticated topics like drug interactions, medication administration, disease diagnoses and doctor recommendations; and assisting general processes such as pharmacy refills, hospital check-in and discharge, and doctor office visits.

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. The term "techniques," for instance, may refer to apparatus(es), system(s), method(s), computer-readable instructions, module(s), algorithms, and/or the like as permitted by the context above and throughout the document.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Overview

Figure 1:
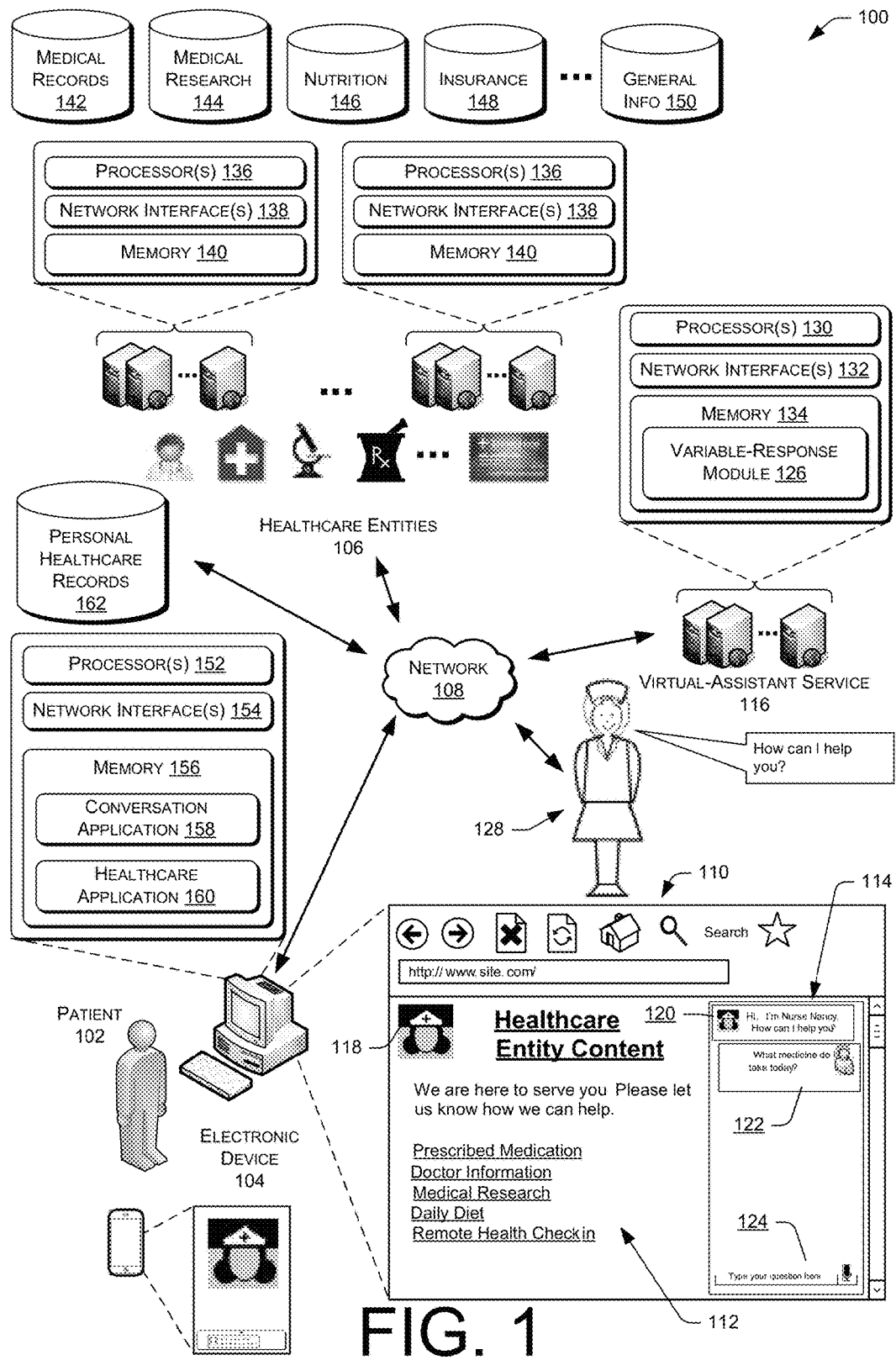
FIG. 1 illustrates an example architecture that includes a patient operating an electronic device to render healthcare provider content. The architecture also includes a virtual-assistant service that provides a virtual healthcare assistant to provide variable responses to patient's inputs. The virtual-assistant service provides a conversation graphical user interface (GUI) that tracks a dialog exchange between the patient and the virtual healthcare assistant.

This disclosure describes techniques for assisting people with their healthcare. The techniques described herein provide for a personal virtual healthcare assistant that engages in dialogs with the patient to help the patient in all facets of healthcare. To facilitate the exchanges between the patient and virtual healthcare assistant, a conversation graphical user interface (GUI) is provide to enable the patient to intuitively understand his/her interactions with the virtual healthcare agent, particularly when speech input is involved.

As noted previously, people are demanding better experiences with smarter devices that understand more of what is being said by them. People are familiar with command-response systems, and simple question-answer systems. The next evolution beyond this is to provide people with devices that engage in conversation. Conversation introduces new complexity in that it not only involves accurately recognizing what words the user is speaking, but also involves reasoning and logic to interpret what the user is saying. Generally, the former issue pertains to improving speech recognition, and the latter pertains to improving natural language processing (NLP). More accurate conversation is achieved through a tight integration of these two technologies—speech recognition and NLP.

Overlay this challenge with the desire and need to accurately provide sophisticated information in the healthcare arena. The patient may be asking about prescriptions, mediation applications, hospital or doctor protocols, medical research, and how to pay bills or use insurance. The virtual healthcare assistant is provided to front end the data aggregation and analysis back ends that manage healthcare information.

The conversation graphical user interface (GUI) may aid the patient by providing a unified interface for accessing information and accomplishing tasks related to healthcare. The virtual assistant may provide functions and responses similar to those of a nurse, receptionist, health coach, dietitian, and the like. The conversation GUI helps the patient access and understand complex information from a variety of sources in a way that is natural for the patient by using speech recognition or NLP or perhaps a combination of the two.

The conversation GUI presents a series of dialog representations, such as speech bubbles exhibiting input from the patient and responses from the virtual assistant. The responses from the virtual assistant may be created by reference to disease management algorithms. For example, if the patient has diabetes and is injecting himself or herself with insulin, the virtual assistant may access an algorithm that indicates where on the body the patient should perform the next injection. Thus, if the patient asked "Where should I inject myself?" the virtual assistant may refer to records indicating where the last injection was performed and the disease management algorithm to determine which location is appropriate for the next insulin injection.

The virtual assistant may effectively follow the patient through all aspects of his or her healthcare. For example, the virtual assistant may facilitate the patient checking in to a hospital or medical facility. Once a diagnosis or treatment plan has been made for the patient, and stored in electronic form accessible to the backend systems, virtual assistant may assist the patient in understanding the diagnosis and/or complying with the treatment plan. For example, the virtual assistant may facilitate the patient submitting medication prescriptions to a pharmacy. Additionally, the virtual assistant may use the prescription information to remind the patient when it is time to take the next dosage of medicine. Moreover, the virtual assistant may track medicines prescribed by different providers and filled at different pharmacies to identify potential drug interactions.

Many aspects of modern healthcare services include dealing with costs and insurance coverage. The virtual assistant may assist in this regard as well. For example, the virtual assistant may calculate estimated costs based on insurance coverage for different treatment options. Additionally, the virtual assistant may facilitate the submitting of claims to an insurance company by assembling the necessary information from other records and querying the patient when additional facts are needed. In some implementations, the virtual assistant may access payment systems such as a mobile payment system or credit card account and allow the patient to provide authorization directly to the virtual assistant which in turn will make payments for healthcare related expenses.

The functioning of the virtual system may include making assumptions about a number of items such as the patient's needs or the patient's intent when generating a query. For example, the assumptions may include parameters used by speech recognition engines to parse the input from the patient, various language models and logic used by NLPs to interpret the patient input, and external factors such as user profiles, learned behavior, and context indicia. Specifically in healthcare related matters, one assumption may be that the patient desires that outcome which is most likely to lead to the best medical result. In some cases, the assumptions may involve use of clarifications so that appropriate assumptions may be derived. For instance, if the patient enters or speaks an input that is ambiguous, the conversation GUI may provide one or more clarifications that seek to have the patient clarify his or her intent.

The conversation GUI may be implemented as part of a system that offers human-like conversation. In some implementations, the system provides virtual assistants that aid patients when interacting with healthcare entities via websites, phone, intranet sites, downloadable client applications, or any other type of platform on which the service provider may provide information to electronic devices. The healthcare provider, meanwhile, may comprise a hospital, clinic, doctor's office, pharmacy, physical therapists, testing laboratory, an insurance agency, a government agency, and/or any type of entity that provides healthcare services of any sort.

In order to identify a response (or "reply") to a particular query from the patient, the techniques may take into account a context associated with the query in two different ways. First, the techniques may take into account the context associated with a query when determining the intent or meaning of the patient's query. In addition, after identifying the patient's intent with use of the context, the techniques may again take this context into account when determining a response or reply to provide back to the patient. In some instances, the techniques take the same pieces of context into account when identifying the intent and the response, while in other instances the techniques may take into account different pieces of context. By taking context into account in both of these ways, the techniques are able to provide responses that more closely emulate human-to-human conversation than when compared to traditional techniques for identifying virtual-assistant responses.

To illustrate, a patient may navigate to a platform of a healthcare entity that includes a virtual assistant. The virtual assistant may include an avatar that resembles a human representative of the service provider (e.g., that represents a human face). In addition, the conversation GUI is provided to facilitate user input. The input may be a command, a statement, a query, an answer, and the like. In some instances, the patient may type the query, while in other instances the patient may provide input audibly, through touch, gesture, or in any other manner. A query may comprise a question (e.g., a patient might ask "When can I see my doctor?" on a hospital website) or may simply comprise one or more keywords or a phrase (e.g., "make an appointment").

In response to receiving the query, the system parses the input and utilizes natural language processing techniques to identify one or more concepts expressed therein. In one example, the concepts may be based at least in part on keywords within the input, although the concepts may additionally be determined using a richer process as discussed below. In one basic example, these concepts may comprise keywords or key phrases, such as "doctor," "appointment," and the like in this example involving a hospital website. After identifying the concept(s) expressed in the input, the techniques may identify a context associated with the input. The context associated with the input may include a context associated with the patient, a context associated with the patient's session on the platform of the healthcare entity, or the like. In some instances, a context is expressed as a value of one or more variables, such as whether or not a patient has a primary care physician (e.g., "primary care physician assigned=true" or "primary care physician assigned=false"). An assumption may be made that the patient wishes to make an appointment with his or her primary care physician unless there is an indication that he or she wishes to see a specialist. A context associated with the input may comprise a value associated with any type of variable that aids in understanding the meaning of a particular query provided by the patient.

After identifying one or more pieces of context, the techniques may map the combination of: (1) the identified concept(s), and (2) the identified piece(s) of context to one of multiple different intents, each of which represents the techniques' best guess as to what exactly the patient is asking about.

After mapping the patient's input to one of multiple different intents based on both the identified concepts and the context associated with the input, the techniques may then map the intent to one of multiple different responses associated with the intent. For example, if the patient generated query about how he or she could improve her health, the intent may be determined to be that the patient wishes to be seen by medical professional or alternatively it may be that the patient is looking for something he or she can do independently. Thus, if the patient wishes to treat his or her diabetes, depending on context, the system may assist the patient and schedule appointment with his or her doctor or recommend nutritional information such as a shopping list for healthy cooking. Thereafter, the techniques may learn the patient's intent in different contexts and use context to more accurately judge the intent of future queries.

In another example, virtual assistant may provide the patient with games or challenges that support cognitive or physical health and are presented in an engaging game-like format. The virtual assistant may engage the patient in trivia games, word games, logic games, or the like to improve the patient's cognitive function. Alternatively, the virtual system may guide the patient through physical tasks such as stretching exercises, walking, etc. and track the patient's progress using GPS or other location detection, the accelerometer within a mobile electronic device, or other techniques. As the patient engages the virtual assistant in the game, the virtual assistant may respond to the patient by providing encouragement or other feedback.

Furthermore, the techniques could connect the patient with other patients having similar health issues or interests as part of a virtual community. The virtual assistant may offer to present the patient's queries to the virtual community to see if another patient has had a similar system situation or has an answer. Information about the patient, such as information obtained from medical devices, may be shared with the virtual community so that the patient can compare his or her health status with that of others. For example, the patient and a friend who are both trying to lower their cholesterol may post their cholesterol numbers and challenge each other to achieve lower cholesterol readings.

As described in detail below, a response provided back to a patient may include content to be presented in the conversation GUI and/or one or more actions. For instance, a response may include content such as a textual answer or information displayed in the dialog representation, an audible answer or information audibly emitted from the user device, one or more hyperlinks to pages that have been determined to be related to the query, or the like. In some instances, the response may include a combination of these. For instance, the returned content may include text and one or more links that are written as a narrative from the perspective of the virtual assistant. This content may also be addressed to or otherwise tailored to the particular user, if recognized. The techniques may also provide information audibly that appears to originate from the virtual assistant.

Additionally or alternatively, the techniques may perform an action on behalf of the patient in response to receiving the query, such as causing a patient's electronic device to navigate to a page deemed related to the query, make an appointment with a medical professional, request a prescription refill on behalf of the patient, submit an insurance claim on behalf of the patient, or the like.

By taking into account the context of a query both: (1) for the purposes of identifying an intent, and (2) after for the purposes of identifying a response identifying the intent, the techniques described herein allow for interaction between virtual assistants and patients that more closely mirror human-to-human interactions.

The conversation GUI is thus described below with reference to an example architecture involving virtual assistants, speech recognition, natural language processing, and other techniques to enhance human-synthesized conversation. It is to be appreciated, however, that other similar and/or different architectures may also implement these techniques.

Example Architecture

FIG. 1 illustrates an example architecture 100 that includes a patient 102 operating an electronic device 104 to render content from one or more healthcare entities 106. The content may comprise a website, an intranet site, a downloaded application, or any other platform on which the patient 102 may access information from the healthcare provider(s) 106. In this example, the patient 102 accesses the platform over a network 108, which may represent any type of communication network, including a local-area network, a wide-area network, the Internet, a wireless network, a wireless wide-area network (WWAN), a cable television network, a telephone network, a cellular communications network, combinations of the foregoing, and/or the like.

As illustrated, the electronic device 104 renders a user interface (UI) 110 that includes content 112 from the healthcare provider 106 and a conversation GUI 114 from a virtual-assistant service 116. In some instances, the conversation GUI 114 may be served from servers of the healthcare provider 106 as part of the platform, while in other instances the conversation GUI 114 may be served from servers of the virtual-assistant service 116 atop of or adjacent to the platform. In either instance, the content 112 of the platform may include any sort of details or information associated with the healthcare provider 106, while the conversation GUI 114 is provided to assist the patient 102 in navigating the content 112 or in any other activity.

The conversation GUI 114 engages the patient 102 in a conversation that emulates human conversation. In some cases, the conversation GUI 114 may include a virtual assistant that has a human-like personality and persona. The virtual assistant may include an avatar 118 that resembles a human, as represented by a picture. The avatar 118 may be an animated character that can take on any number of shapes and appearances, and resembles a human talking to the patient 102. The avatar 118 may be arranged as a representative of the service provider 106, and hence be associated with the content 112 as shown. Alternatively, the avatar 118 may be a dedicated personal assistant to the patient 102, and hence be associated with the conversation GUI 114, either as part of the panel area or elsewhere in the UI 110, but displayed in association with the conversation GUI 114.

The conversation GUI 114 conveys a visual representation of a conversation between the patient 102 and the avatar 118 (or virtual-assistant service 116). The conversation GUI 114 presents a series of dialog representations 120 and 122, such as graphical content bubbles, which are designated as representing dialogue from either the patient 102 or the avatar 118. In this illustration, the patient-originated dialog representations 122 contain input from the patient 102 (verbal or otherwise) and the device- or avatar-originated dialog representations 120 contain responses from the device or virtual assistant. The representations 120 and 122 may be offset in the conversation GUI 114 to visually convey which entity is associated with the content. Here, the assistant-originated dialog representation 120 is offset to the left, whereas the patient-originated dialog representation 122 is offset to the right. The conversation GUI 114 may also includes an interface area 124 that captures input from the patient 102, including via typed input, audio or speech input, as well as touch input and gesture input. Gesture or emotive input may be captured if the electronic device 104 is equipped with a camera or other sensor.

As noted above, the patient 102 may enter a query into the interface area 124 of the conversation GUI 114. The electronic device 104 transmits this query over the network 108 to the virtual-assistant service 116. In response, a variable-response module 126 of the virtual-assistant service 116 may identify a response to provide to the patient 102 at least partly via the virtual assistant. For instance, the variable-response module 126 may map a query from the patient 102 to an intent based on a context of the query and may then map the intent to a response, again with reference to the context of the query. After identifying the response, the virtual-assistant service 116 and/or the healthcare provider 106 may provide the response the electronic device 104 for presentation to the patient 102. The response may be added to a dialog representation of the conversation GUI 114 and/or audibly played to the patient 102. Additionally, the variable-response module 126 may identify situations in which the virtual assistant is unable to respond. In these situations the variable-response module 126 may forward the conversation to a human assistant 128 who can continue the conversation with the patient 102.

As illustrated, the virtual-assistant service 116 may comprise one or more computing devices (e.g., one or more servers) that include or otherwise have access to one or more processors 130, one or more network interfaces 132, and memory 134, which stores the variable-response module 126. The healthcare provider 106, meanwhile, may comprise one or more computing devices (e.g., one or more servers) that include or otherwise have access to one or more processors 136, one or more network interfaces 138, and memory 140, which stores or has access to medical records 142 of the patient 102, medical research 144, nutrition information 146, insurance information 148, and/or general information 150.

Finally, the electronic device 104 of the patient 102 may include or otherwise have access to one or more processors 152, one or more network interfaces 154, and memory 156, which stores a conversation application 158 for rendering the UI 110 and a healthcare application 160 for providing information from the healthcare provider 106 to the patient 102. The client application may comprise a browser for rendering a site, a downloaded application provided by the healthcare provider 106, or any other client application configured to output content from the healthcare provider 106. While FIG. 1 illustrates the service provider 106 storing the medical records 142, medical research 144, nutrition information 146, and insurance information 148, in some instances the healthcare application 160 may store some or all of this content locally on the device 104.

Furthermore, while FIG. 1 illustrates the electronic device 104 as a desktop computer, the electronic device 104 may comprise any sort of device, such as a mobile phone, a multifunctional device, a laptop computer, a tablet computer, a personal digital assistant (PDA), or the like. In each instance, the electronic device 104 may include various additional components, such as one or more output devices (e.g., displays, speakers, etc.), one or more input devices (e.g., a keyboard, a touchscreen, etc.), an operating system, system busses, and the like.

The various memories 132, 140, and 156 store modules and data, and may include volatile and/or nonvolatile memory, removable and/or non-removable media, and the like, which may be implemented in any method or technology for storage of information, such as computer-readable instructions, data structures, program modules, or other data. Such memory includes, but is not limited to, RAM, ROM, EEPROM, flash memory or other memory technology, CD-ROM, digital versatile disks (DVD) or other optical storage, magnetic cassettes, magnetic tape, magnetic disk storage, or other magnetic storage devices, RAID storage systems, or any other tangible medium which can be used to store the desired information and which can be accessed by a computing device.

The patient 102 may also directly access his or her personal healthcare records 162 by use of the electronic device 104. The personal healthcare records 162 may contain information entered by one of the healthcare entities 106 or by the patient 102. For example, if a healthcare entity 106 provides information to the patient 102 only in paper form (e.g., a hardcopy) the patient 102 may manually enter that information into his or her personal healthcare records 162. The conversation GUI 114 may provide the interface for entering information into the personal healthcare records 162 and may assist the patient 102 in providing complete information as well as suggesting an appropriate category or location within the personal healthcare records 162 to store the manually-entered information.

While FIG. 1 illustrates one example architecture for providing variable responses regarding healthcare information, it is to be appreciated that multiple other architectures may implement the described techniques. For instance, while FIG. 1 illustrates the healthcare entity 106 as separate from the virtual-assistant service 116, in some instances some or all of these components may reside in a common location, spread out amongst multiple additional entities, located on the electronic device 104, and/or the like.

Example Variable Responses

Figure 2A:
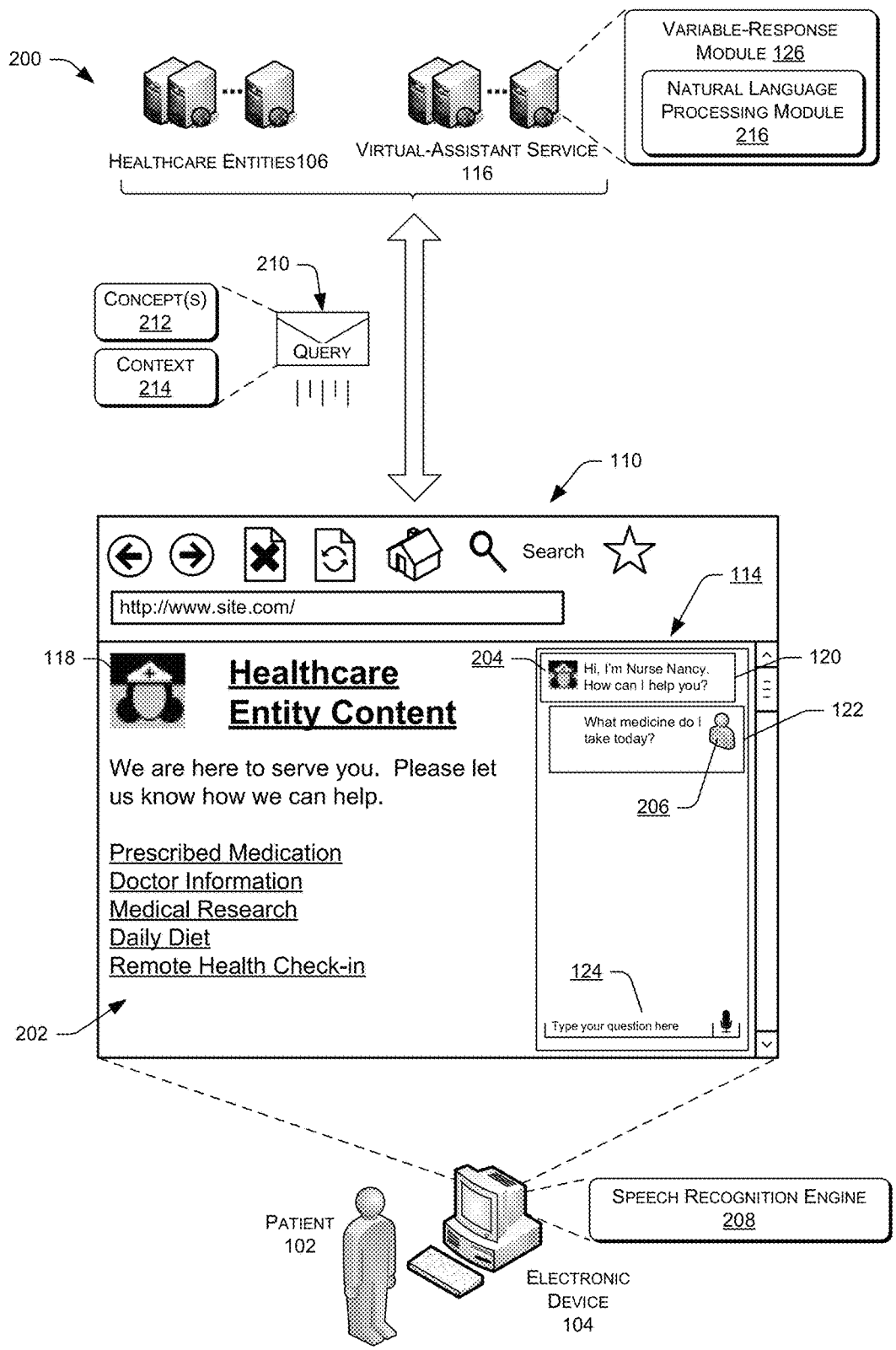
FIGS. 2A-B collectively illustrate a high-level communication flow between an electronic device of the patient and the healthcare provider and/or the virtual-assistant service. The figures illustrate the conversation GUI and formation of dialog representations of patient inputs and responses of the virtual healthcare assistant in a scenario involving directing a patient in taking medication.
Figure 2B:
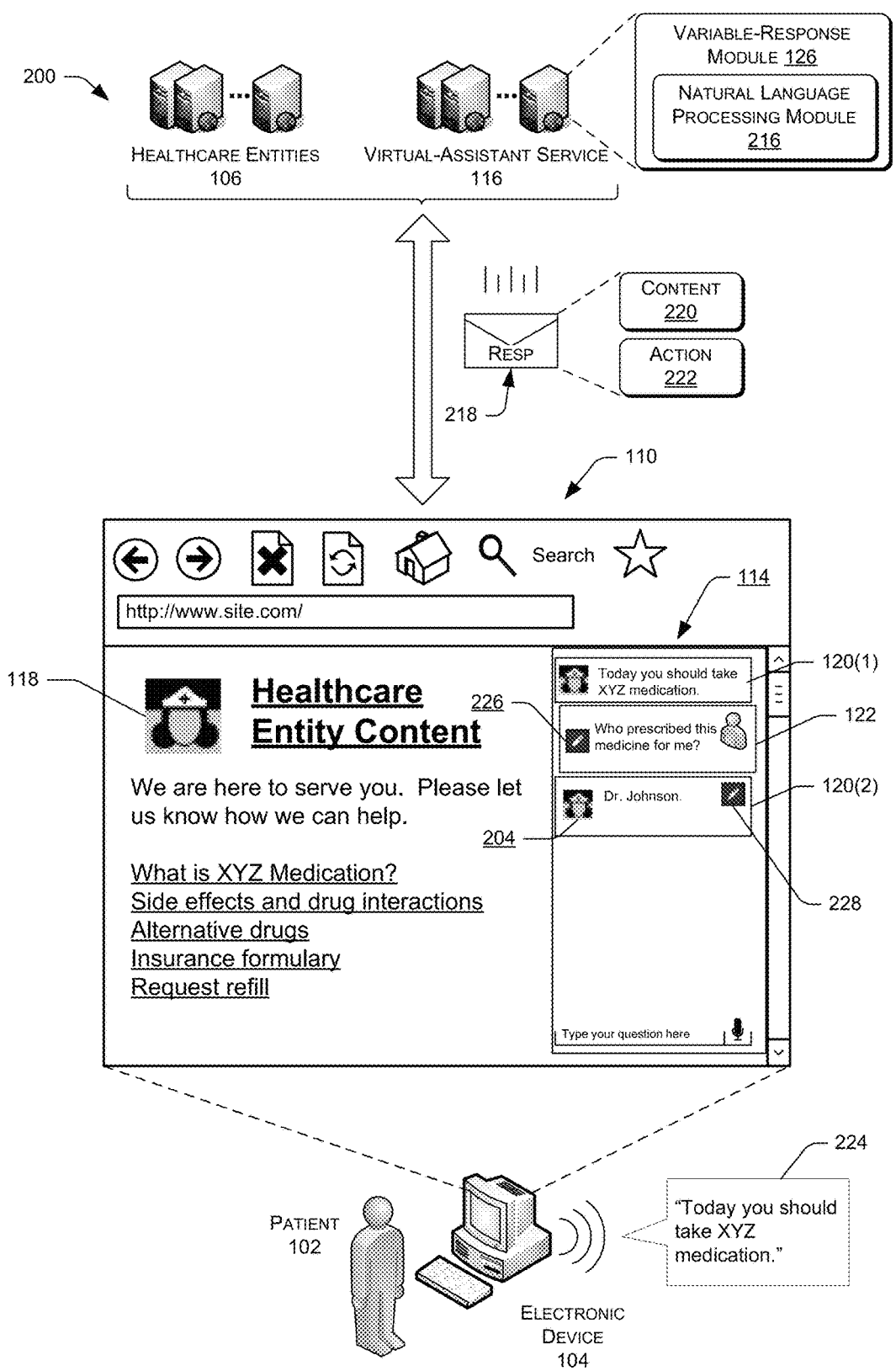

FIGS. 2A-B collectively illustrate a high-level communication flow 200 between the example electronic device 104 of the patient 102 and the healthcare entity 106 and/or the virtual-assistant service 116. As illustrated, the electronic device 104 renders a user interface (UI) 110 that includes a virtual assistant avatar 118 and content 202 from the healthcare entity 106 and the conversation GUI 114 from the virtual-assistant service 116. In some instances, the virtual-assistant service 116 serves the conversation GUI 114 to the device 104, while in other instances the healthcare entity 106 serves the conversation GUI 114, either as part of the content 202 or after receiving the conversation GUI 114 from a separate virtual-assistant service 116.

In either instance, the content 202 here represents a home page of an example healthcare entity. The content includes a title of the page, a welcome statement, and links to possible service offerings (e.g., Prescribed Medication, Medical Research, etc.).

The conversation GUI 114 emulates human-to-human interaction between the patient 102 and the healthcare entity 106. In this example, the conversation GUI 114 includes one or more assistant-originated dialog representations 120 associated with the healthcare entity, and these representations 120 include a small image of the virtual assistant 204. The virtual assistant image 204 may be associated with the healthcare entity, as above, or alternatively as a personal digital assistant personalized for the patient 102. In this illustration, the virtual assistant 118 initiates the conversation (e.g., "Hi, I'm Nancy. How can I help you?") as represented by the top most dialog representation in the conversation GUI 114.

The conversation GUI 114 also includes one or more user-originated dialog representations 122 associated with the healthcare entity, and these representations 122 include a small image 206 of the patient 102. This user-originated dialog representation 122 is presented as part of the conversation GUI 114 in response to the patient 102 entering a query in the entry area 124. In this example, the patient input is a question, "What medicine do I take today?" The patient 102 may have typed the question or verbally asked the question. The query may be entered and submitted by hitting a return key, actuating a control icon (not shown), or by any other mechanism. The dialog representation 122 may appear in the conversation GUI 114 upon entry of the query as illustrated here. Alternatively, the dialog representation 122 may appear in concert with the responsive dialog representation that is returned from the virtual-assistant service 116.

In the case of verbal input, the electronic device 104 may include a speech recognition engine 208 that receives the vocal audio data captured by a microphone. The speech recognition engine 208 may convert the audio to digital information, optionally computes a frequency transform, and identify parts of speech for use in deciphering the speech of the patient 102. The speech recognition engine 208 may also function to authenticate an identity of the patient 102 through analysis of the voice patterns contained in the verbal input. Thus, when the patient 102 provide spoken commands to the electronic device 104 it may be unnecessary to perform additional authentication checks such as asking for a password. This increases the convenience for the patient 102 and using the biometric properties of the patient's voice may provide a higher level of security for sensitive medical information than traditional password protection.

The speech recognition engine 208 may be equipped with additional algorithms for understand the speech of the patient 102 when his or her voice is modified by health condition such as a stuffy nose caused by a cold. Additionally, the speech recognition engine 208 may have further algorithms to detect the effects of pain on speech patterns of the patient 102. If it is detected that the patient 102 is in pain, this information may be used as context for interpreting queries and instructions from the patient 102. In some implementations, the speech recognition engine 208 may reside at the virtual assistant 116, while in other implementations, functionality in the speech recognition engine 208 is distributed at the electronic device 104 and virtual-assistant service 116. In other implementations, the speech recognition engine 208 may be a third party service that is leveraged by the virtual-assistant service 116 and/or the electronic device 104.

In some instances, the electronic device 104 provides a query 210 directly to the healthcare entity 106, which identifies an appropriate response and may provide this response back to the electronic device 104 or to another device associated with the patient 102. In other instances, the healthcare entity 106 may receive the query 210, provide the query 210 to the virtual-assistant service 116, receive a response from the service 116, and provide the response to the electronic device 104 or to another device associated with the patient 102. In still other instances, the electronic device 104 provides the query 210 to the virtual-assistant service 116 directly, which may identify a response or provide the query 210 to the healthcare entity 106 for identifying a response. The virtual-assistant service 116 or the healthcare entity 106 may then provide the response to the electronic device 104 or to another device associated with the patient 102. Of course, while a few example communication flows have been described, it is to be appreciated that other communication flows are possible.

In each instance, the query 210 sent to the healthcare entity 106 and/or the virtual-assistant service 116 may comprise the words and phrases within the string of text entered by the patient 102, from which concepts 212 may be derived. In some implementations, the concepts 212 may be derived at least partly by the electronic device 104 through some natural language pre-preprocessing. In other implementations, the concepts may be derived as part of the virtual-assistant service 116 or a combination of the device and service.

The query 210 sent to the healthcare entity 106 and/or the virtual-assistant service 116 may further comprise one or more pieces of context 214. The context 214 may be based on any additional factors associated with the patient 102, the electronic device 104, or the like. As described above, for instance, the context 214 may include whether or not the patient 102 is signed in with the healthcare entity 106, a health status of the patient 102, an age of the patient 102, a type of device medical device used by the patient 102, or the like.

The query 210 is handled by the variable-response module 126. A natural language processing (NLP) module 216 is provided as part of the variable-response module 126. The NLP module 216 receives the speech parts output by the speech recognition engine 208 and attempts to order them into logical words and phrases. The NLP module 216 may employ one or more language models to aid in this interpretation. The variable-response module 126 ultimately processes a response to be returned to the electronic device 104.

FIG. 2B continues the illustration and represents the healthcare entity 106 and/or the virtual-assistant service 116 providing a response 218 for output on the electronic device 104 or on another device associated with the patient 102. As described above and in further detail below, the healthcare entity 106 and/or the virtual-assistant service 116 may have identified the response by first mapping the concepts 212 and the context 214 to an intent, and thereafter mapping the intent and the context 214 to the response 218. As illustrated, the response 218 may comprise content 220, one or more actions 222 to perform, or a combination thereof.

Upon receipt of the response 218, the conversation GUI 114 is refreshed or updated to include the content 220 from the response 218. The content 220 may be provided as one of the textual-based dialog representations. For example, a new assistant-originated dialog representation 120(1) is added to the dialog panel and visually associated with the virtual assistant through the left-side orientation and the image 204. The dialog representation 120(1) provides a response to the patient's previous query. The response may be based on medical records or prescription information associated with the patient 102. This is the second dialog representation is associated with the virtual assistant. As noted above, the user-originated dialog representation 122 may be presented together with the response, if not already part of the dialog panel. In addition to a text display as part of the conversation GUI 114, the response may also be audibly provided to the user, as represented by the audible output 224.

The conversation between the virtual assistant and the patient 102 may continue. The patient 102 my next ask "Who prescribed this medicine for me?" which appears in the conversation GUI 114 as dialog box 122. In response the healthcare entity 106 may access records associated with the prescription and identify that the prescribing doctor is Dr. Johnson. This information is returned in a subsequent dialog box 120(2) from the virtual assistant. If the patient 102 has further questions the dialogue in the conversation GUI 114 may continue.

The actions 222 included in the response may vary widely in type and purpose. Example actions 222 might include requesting a medication refill on behalf of the patient 102, setting an appointment reminder to remind the patient 102 to pick up a medication refill, initiating a communication on behalf of the patient 102 to a doctor's office in order to request updated prescription information, or another type of action.

Example Conversation GUI

Within continuing reference to FIG. 2B, notice that two of the dialog representations 122 and 120(2) contain respective controls 226 and 228 positioned in association with the text display. The controls 226 and 228 may have any associated icon, and is actionable by mouse click or other mechanisms. The controls 226 and 228 enable the patient 102 to interact with the conversation GUI 114 in a way to ascertain how dialog portions were assembled. That is, through use of the controls, the patient 102 can evaluate what assumptions went into understanding the input and how the response was determined. By revealing these assumptions in an intuitive user interface, the patient 102 can quickly ascertain, for example, whether the virtual assistant misunderstood the input due to a potential misrecognition by the speech recognition engine or whether the user input was misinterpreted by the NLP module. The conversation GUI 114 then allows the patient 102 to modify those assumptions used to determine the response.

Figure 3:
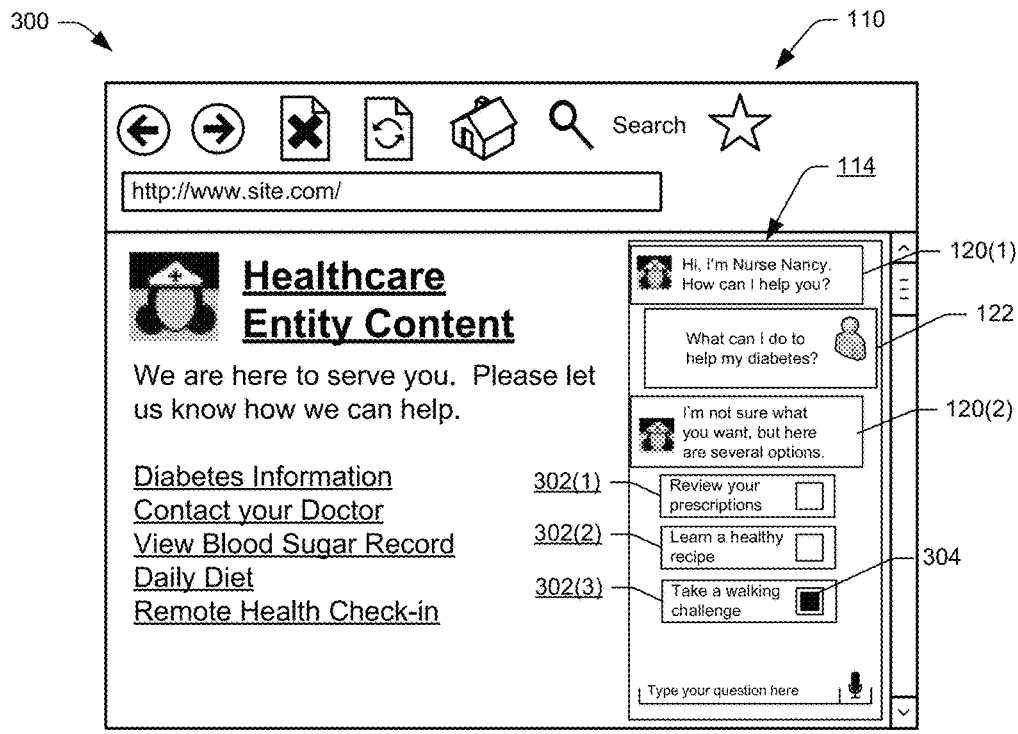
FIG. 3 shows the conversation GUI at an instance when the patient provides an ambiguous input and the virtual assistant seeks to clarify what the patient meant in the preceding input.

FIG. 3 shows an instance 300 of the UI 110 that is presented in response to an ambiguous query from the patient 102. Dialog representation 122 includes a query that the virtual-assistant service 116 cannot process unambiguously. The virtual assistant responds with dialog representation 120(2) indicating the ambiguity and providing the patient 102 with several possible options 302. Here, there are three possible options 302(1), 302(2), and 302(3), although there may be a different number of options in other scenarios. In this scenario, the patient 102 selects the third option 302(3) to take a walking challenge. The patient 102 can select this element 302(3) in a number of ways. The patient 102 can mouse over the element 302(3) and select it, or on a touch screen device, can simply touch the appropriate box. Alternatively, the patient 102 can use a keyboard or keypad to select the appropriate one, or modify the existing input either with the keyboard or verbally. Icon 304 informs the patient 102 of these options, and upon selection, receive the user input.

For purposes of ongoing discussion, suppose the patient 102 selects the third clarification element 302(3) to clarify that he or she wishes to engage in a walking challenge. The walking challenge may be a type of physical game in which the patient 102 engages in an activity, here walking, that is recommended by the virtual assistant as appropriate for the patient's health needs.

Figure 4:
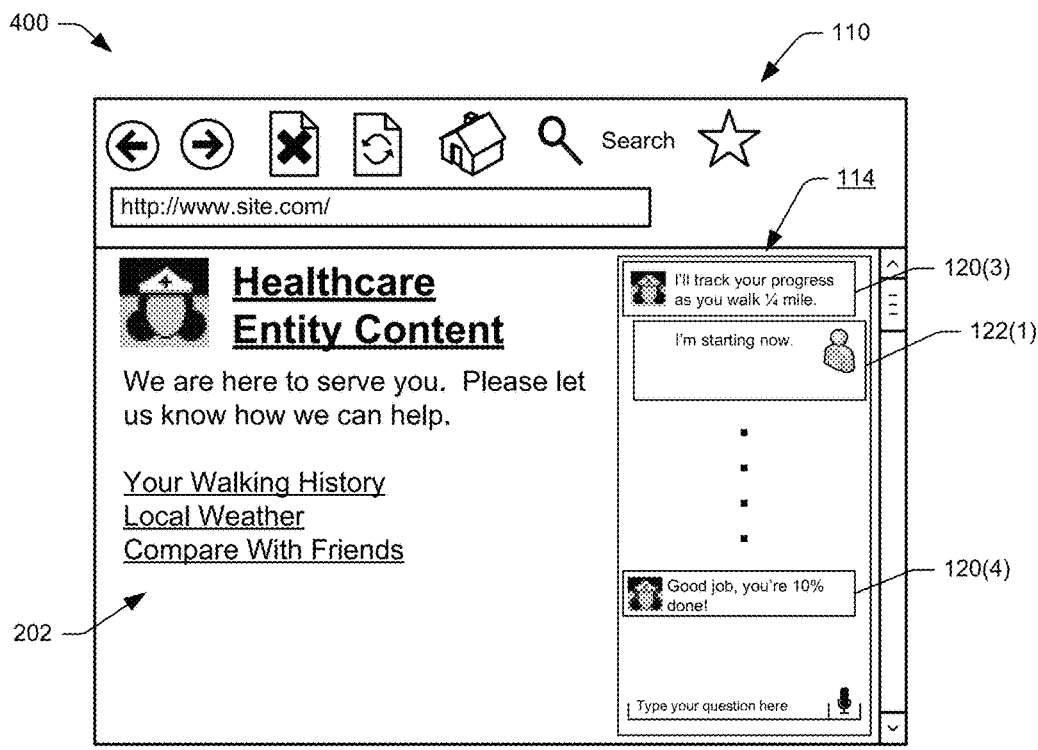
FIG. 4 shows the conversation GUI at an instance after that shown in FIG. 3, to illustrate a modified dialog representation in which the patient receives encouragement from the virtual assistant while participating in a game or activity.

FIG. 4 shows an instance 400 of the UI 110 that is presented in response to patient's selection of the clarification element 302(3) in the conversation GUI 114. The content 202 presented in the UI 110 may change based on the dialogue occurring in the conversation GUI 114. Here, the patient 102 has selected a walking challenge, so the content 202 provides information about the patient's past walking activities, weather in case the patient 102 wishes to walk outside, and possibly a social connection in which the patient 102 can share his or her walking information with friends.

The next dialog representation from the virtual assistant 120(3) provides an explanation of the game to the patient 102. The patient 102 may reply to the virtual assistant as he or she engages in the game. Here, the dialog representation 122(1) from the patient, indicates that he or she is starting the game activity. If, for example, the UI 110 is represented in a mobile device, the mobile device may include location awareness to track the distance that the patient 102 is walking. In this implementation, the virtual assistant may provide feedback to the patient 102 as shown in the dialog representation 120(4) that encourages the patient 102 and informs the patient 102 of his or her progress.

Figure 5:
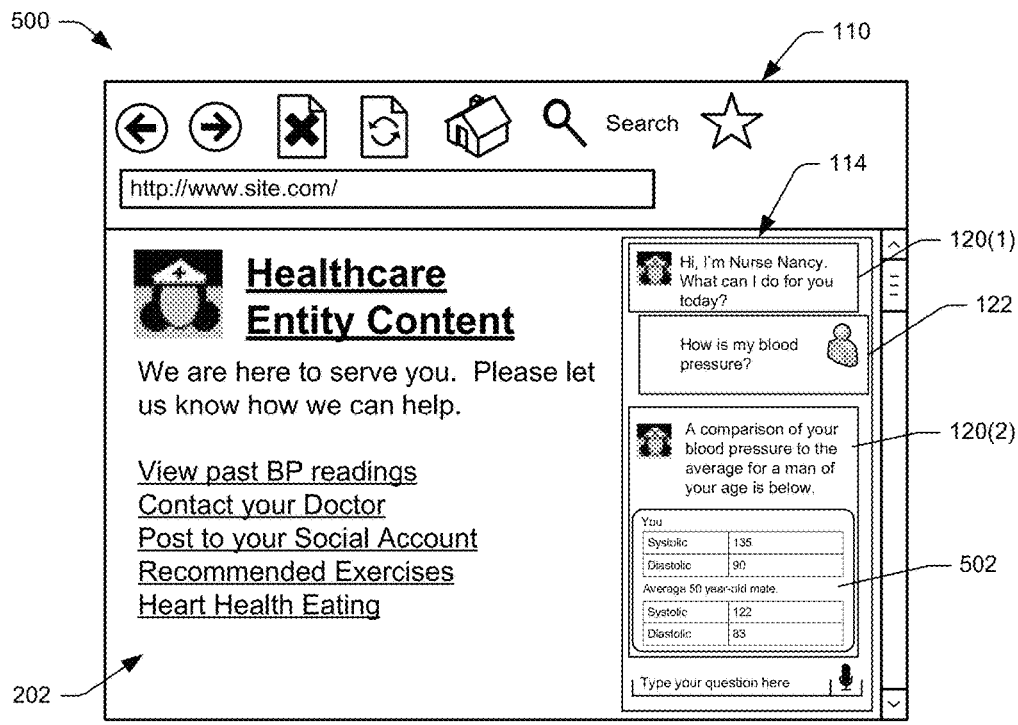
FIG. 5 shows the conversation GUI presenting a comparison between the blood pressure of the patient and an average person.

FIG. 5 shows an instance 500 of the UI 110 that provides the patient a comparison between his or her health information and health information of an average or typical person. The conversation GUI 114 displays conversational bubbles as discussed above. Here, the patient 102 communicates in dialog representation 122 a query about his or her blood pressure. In response, the dialog representation 120(2) from the virtual assistant may access the patient's blood pressure record either from stored records or if the patient 102 is currently connected to a medical device that measures blood pressure directly from that medical device through an appropriate interface. The comparative health information or health metrics may be provided in the conversation GUI 114 shown here as element 502. The comparison may also be provided elsewhere in the UI 110 such as with the content 202.

Figure 6:
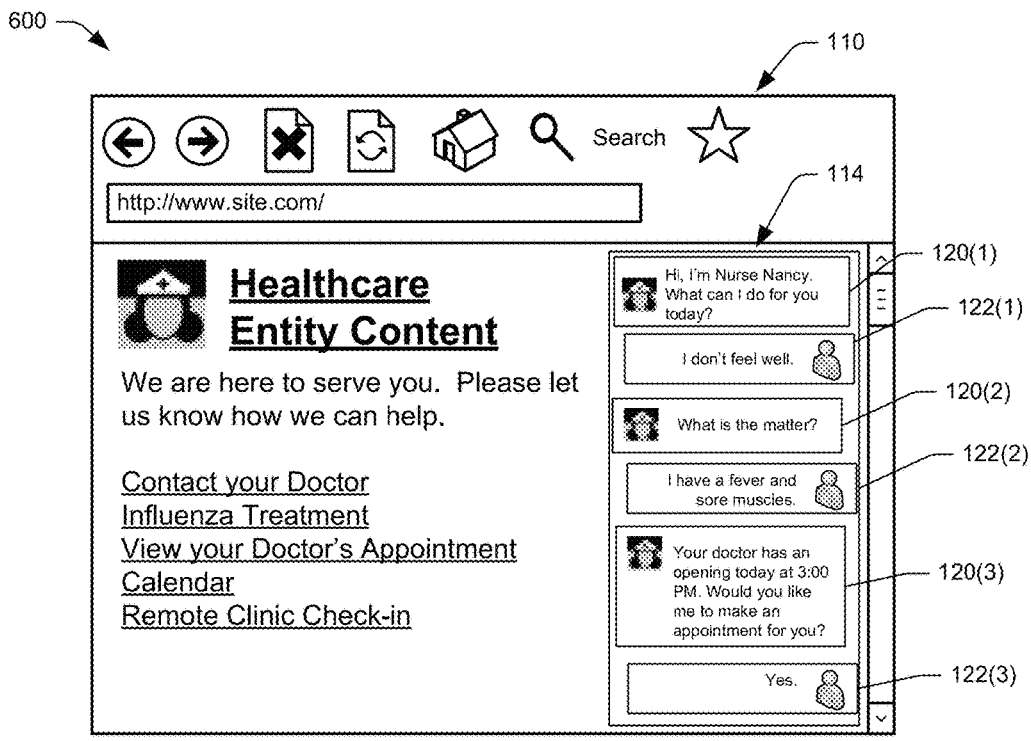
FIG. 6 shows the conversation GUI during the interaction between the virtual assistant and the patient in which the virtual assistant helps the patient make a medical appointment.

FIG. 6 shows an instance 600 of the UI 110 that provides appointment scheduling functionality from within the conversation GUI 114. An example dialog between the patient 102 and the virtual assistant is represented with the dialog bubbles 120 and 122. A response from the patient 102 in dialog representation 122(2) may provide the backend systems with sufficient information to make a preliminary diagnosis of the possible ailment of the patient 102. Here, the indication of a fever and sore muscles may suggest influenza. If the indication from the patient was of a different type of problem such as bleeding, problems breathing, other symptoms that suggests a more serious medical problem the virtual assistant may recommend that the patient 102 call for emergency medical assistance, or alternatively if the electronic device 104 has telephone capabilities the virtual assistant may offer to initiate the phone call on behalf of the patient 102.

In addition to providing a basic level of diagnosis, the backend system supporting the virtual assistant may also access scheduling functionality for medical professionals. The medical records of the patient 102 may identify the patient's doctor and the virtual assistant may proactively access the schedule of the doctor to see when the patient 102 could make an appointment. The virtual assistant may communicate this information obtained from the patient's medical records and/or from a scheduling system of the doctor's office in the dialog representation 120(3). This is one example of how the virtual assistant may integrate information from multiple sources to provide the patient 102 convenient access to healthcare related information through a conversation GUI 114.

Figure 7A:
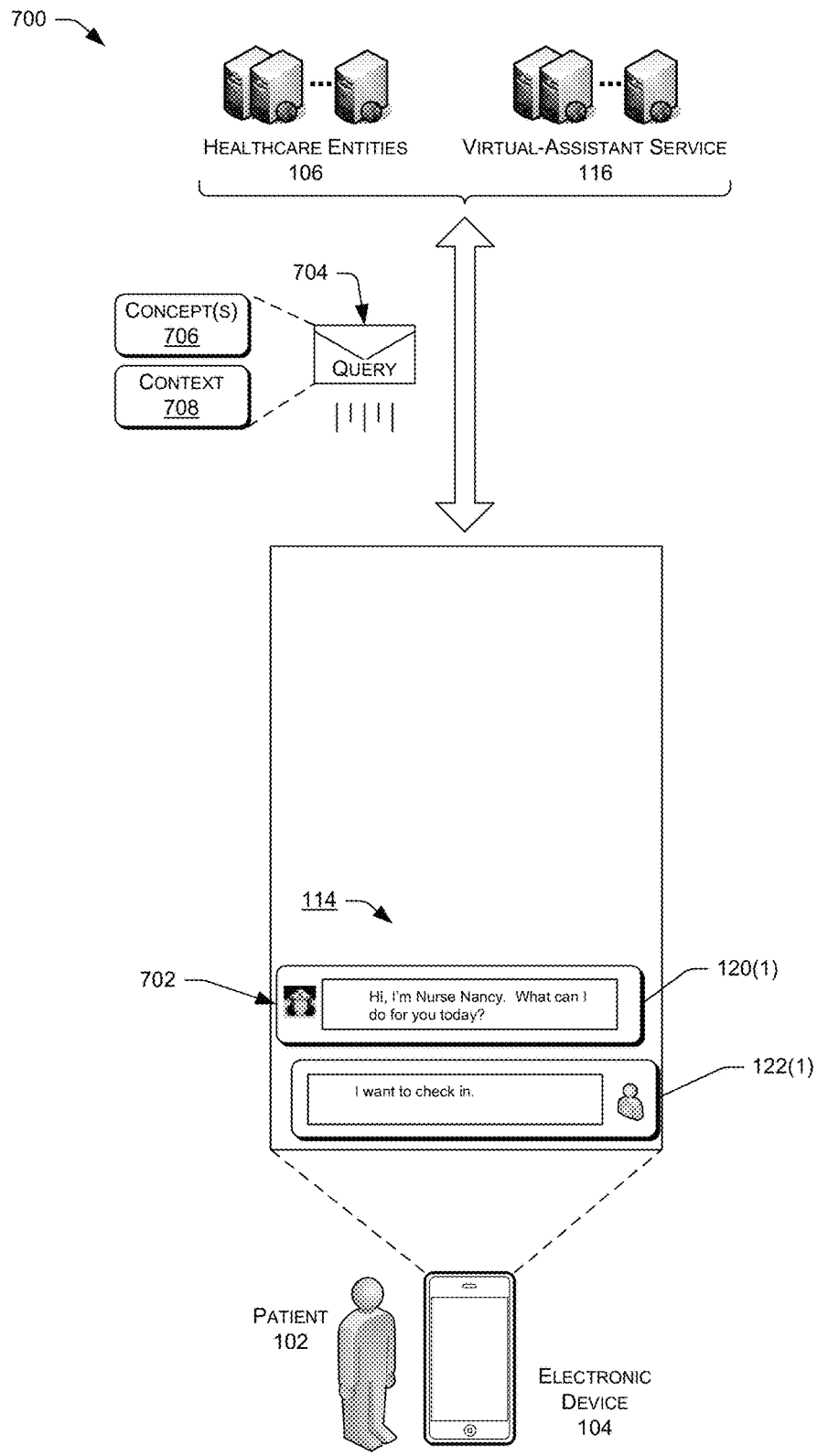
FIGS. 7A-B collectively illustrate a high-level communication flow between an electronic device of the patient and the healthcare provider and/or the virtual-assistant service. The figures illustrate the conversation GUI and formation of dialog representations of patient inputs and responses of the virtual healthcare assistant in a scenario involving assisting the patient in checking in at a doctor's office.
Figure 7B:
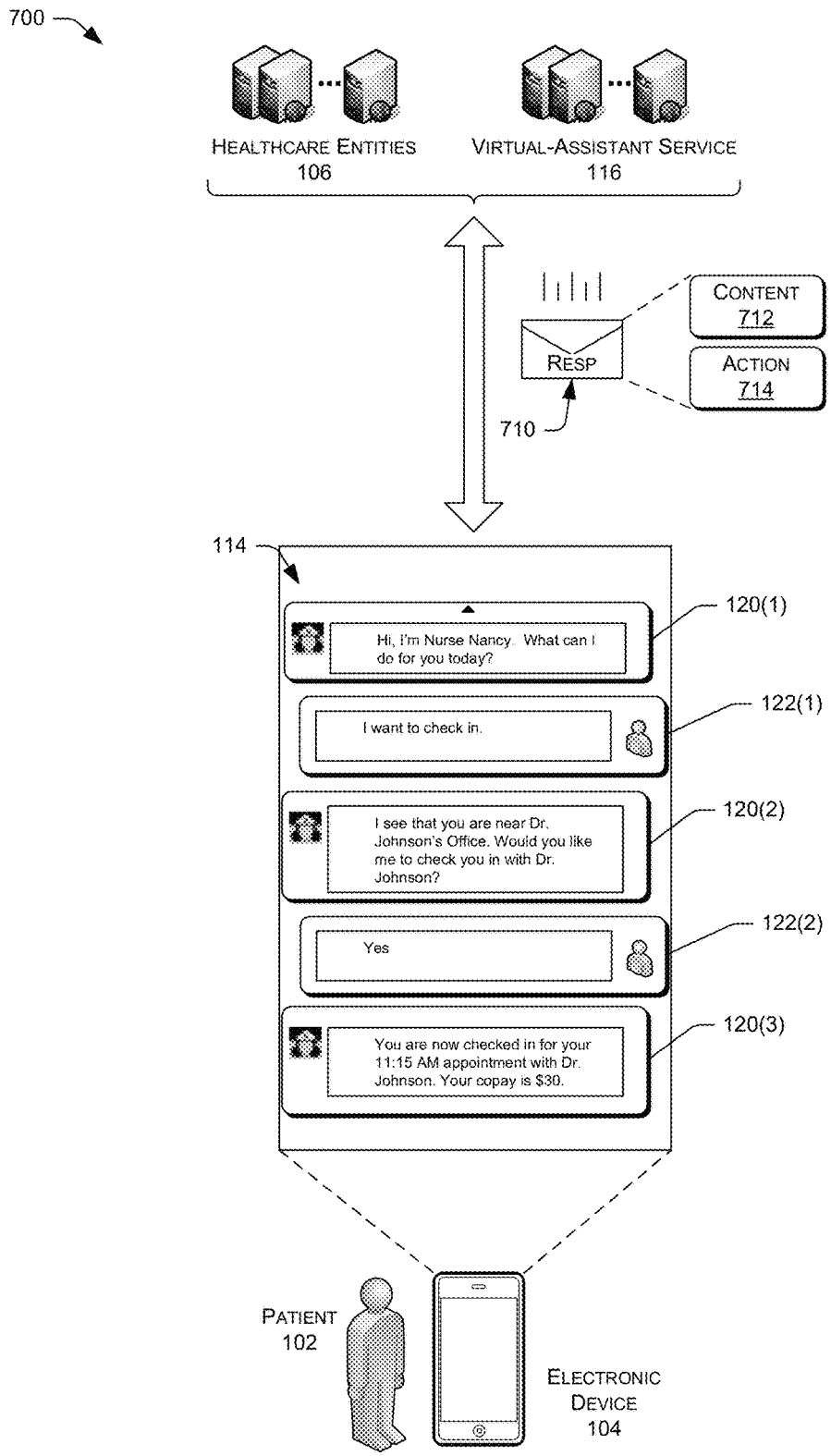

FIGS. 7A-B collectively illustrate another implementation 700 involving the electronic device 104 implemented as a mobile device. This implementation 700 shows a high-level communication flow between the electronic device 104 of the patient 102 and the healthcare entity 106 and/or the virtual-assistant service 116. As shown in FIG. 7A, the virtual assistant is the main, and perhaps only, persona 702 on the initial UI of the electronic device 104. The virtual assistant may be part of the operating system of the electronic device 104 to give the electronic device 104 a personality. Alternatively, the virtual assistant may be an application that is stored and executed on the electronic device 104. The electronic device 104 may include multiple virtual assistant personas 702 such as "Nurse Nancy" for interacting with healthcare entities and another persona for scheduling airline travel, etc. The conversation GUI 114 may be provided initially at the lower portion of the display area of the electronic device 104. Suppose the patient 102 provides instructions to the electronic device 104 shown in dialog representation 122(1). The instructions may be processed as a query 704 which is communicated to the healthcare entity 106 and/or the virtual-assistant service 116 as a combination of one or more concepts 706 and one or more pieces of context 708.

The instructions, "I want to check in." includes the concept 706 of checking in and registering, but the target of this action is not explicitly specified by the patient 102. The response is developed by the virtual-assistant service 116 through use of the context 708 as discussed in FIG. 7B.

FIG. 7B provides an illustration of implementation 700 at a later point in time. Upon receiving the query 704, the healthcare entity 106 and/or the virtual-assistant service 116 may determine a suitable response 710 to provide to the patient 102. Again, this response may be determined by identifying an intent of the query 704 with reference to the concepts 706 and one or more pieces of the context 708, and then by mapping the determined intent along with one or more same or different pieces of the context 708 to produce the response 710. For example, the geolocation of the electronic device 104 may be one piece of context 708. Thus, the ambiguous instruction to "check in" may have meaning when interpreted in light of the context 708 because the virtual-assistant service 116 and/or the healthcare entity 106 may infer that the patient 102 wishes to check in at the healthcare provider's office located nearest to the current location of the electronic device 104. The dialog representation 120(2) may represent this determination and the virtual assistant may ask the patient 102 for confirmation of the inference (i.e. that the patient 102 wishes to check in to Dr. Johnson's office).

The response 710 may comprise content 712 and/or an action 714. The response content 712 may be presented to the patient 102 via the conversation GUI 114 and/or audibly output by the electronic device 104. The action 714 may be checking the patient 102 in to Dr. Johnson's office for a previously scheduled appointment. The conversation GUI 114 provides a confirmation of this action 714 in dialog representation 120(3). The existence of the appointment and a specific time for the appointment may be obtained by accessing scheduling records. Additionally, the virtual assistant may provide the patient 102 with insurance information relevant to the appointment such as the amount of a copayment.

Example Virtual-Assistant Service

Figure 8:
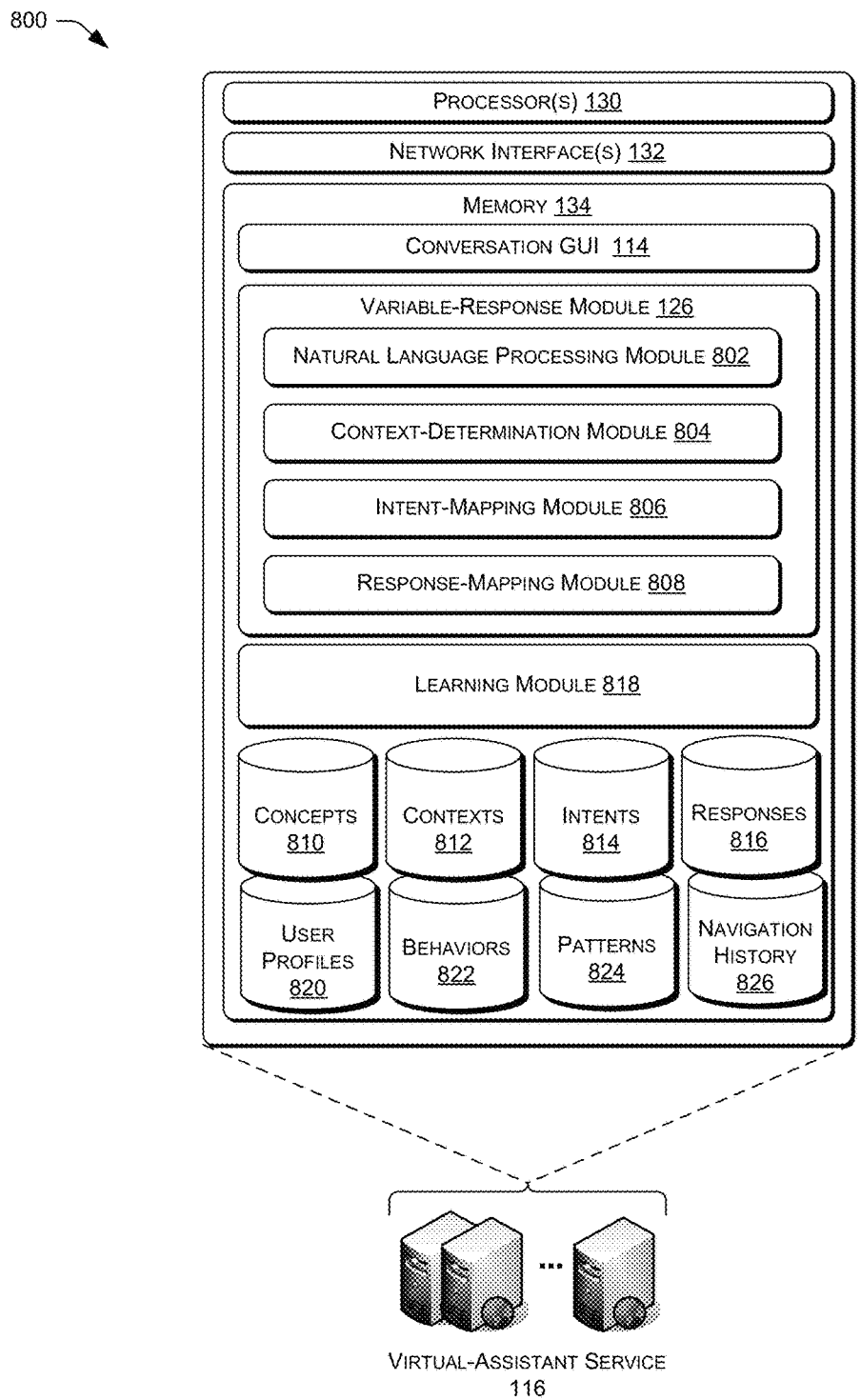
FIG. 8 illustrates example components that the virtual-assistant service of FIG. 1 may utilize when determining a response to the input.

FIG. 8 illustrates example components that the virtual-assistant service 116 may utilize when determining a response to the patient's input. As illustrated, the virtual-assistant service 116 may be hosted on one or more servers that include one or more processors 130, one or more network interfaces 132, and memory 134.

The memory 134 may store or otherwise have access to the conversation GUI 114 and the variable-response module 126. The variable-response module 126 may include a natural language processing module 802, a context-determination module 804, an intent-mapping module 806, and a response-mapping module 808. In addition, the memory 134 may also store or otherwise have access to a datastore of one or more concepts 810, a datastore of one or more contexts 812, a datastore of one or more intents 814, and a datastore of one or more responses 816.

The natural language processing (NLP) module 802 may implement known or new natural language processing techniques to parse a received query for the purpose of identifying one or more concepts expressed therein. For instance, the NLP module 802 may identify a set of concepts 810 based on the string of text of the query. The context-determination module 804, meanwhile, may function to identify one or more pieces of context associated with the received query, such as whether the patient is signed in, a geolocation of the patient when issuing the query, or the like. The intent-mapping module 806 may then map the identified set of concepts and the identified pieces of context to one of the multiple different intents 814. That is, given the union of a particular concept set and respective values of one or more variables associated with the context of the query, the intent-mapping module 806 may map the query to a particular intent of the intents 814.

Finally, the response-mapping module 808 may map the intent to a particular response based at least in part on respective values of one or more variables, which may be the same or different variables used when mapping the query to an intent. Stated otherwise, and as illustrated below with reference to FIG. 10, each intent of the intents 814 may be associated with multiple different responses. Therefore, after a particular query has been mapped to a particular intent, the response-mapping module 808 may identify which of the multiple responses associated with the intent to provide to the patient who provided the query, with reference to the context of the query.

The virtual-assistant service 116 may further implement a learning module 818, which is shown stored in the memory 134 for executing on the processor(s) 130. The learning module 818 observes patient activity and attempts to learn characteristics about the patient that can be used as input to the variable-response module 126. The learning module 818 may initially access a user profile datastore 820 to find any preferences that the patient may have provided. Then, over-time, the learning module 818 may learn any number of characteristics about the patient, such as health status (generally healthy or very sick), treatment regimens of the patient (e.g., dialysis, chemotherapy, etc.), a current location of the patient, insurance eligibility for particular procedures, and the like. Some characteristics about the patient may be behaviors engaged in by the patient such as tending to arrive late for appointments, traveling to locations where vaccination is recommended, etc. The patient behaviors are stored in a behavior datastore 822.

The learning module 818 may also track patterns (e.g., patient has been losing weight over the last year, patient's blood pressure is higher when at work, etc.). Patterns may be kept in the patterns store 824. The learning module 818 may also monitor navigation history, which is maintained in the store 826. Each of these observed behaviors, patterns, and navigation history may be useful to the variable-response module 126 by providing additional context to the input of the patient.

As an example of the learning, consider the scenario above where the patient asked "What can I do to help my diabetes?" The virtual assistant provided multiple options from which the patient selected a walking challenge. The learning module 818 can record this selection. Thus, when the patient next asks about helping his or her diabetes or other medical condition, the intent-mapping module 806 may use information from the learning module 818 to provide a game or other physical activity as the first option to the patient.

As a second example, consider a query from the patient asking "How do I treat my code?" Even though the speech recognition might correctly process the verbal input when the patient is speaking a normal voice, the learning module 118 may recognize from past input that "code" can mean "cold" when the patient has a stuffed up nose. The virtual assistant service 116 will use the learned correction and make a new assumption that the patient means "cold" and additionally obtain the piece of context indicating that one of the patient's symptoms is a stuffy nose.

While FIG. 8 illustrates the described components as residing on the virtual-assistant service 116, in other instances some or all of these components may reside in another location. For instance, these components may reside in whole or part on each of the virtual-assistant service 116, the healthcare entity 106, the electronic device 104, or at any other location.

Figure 9:
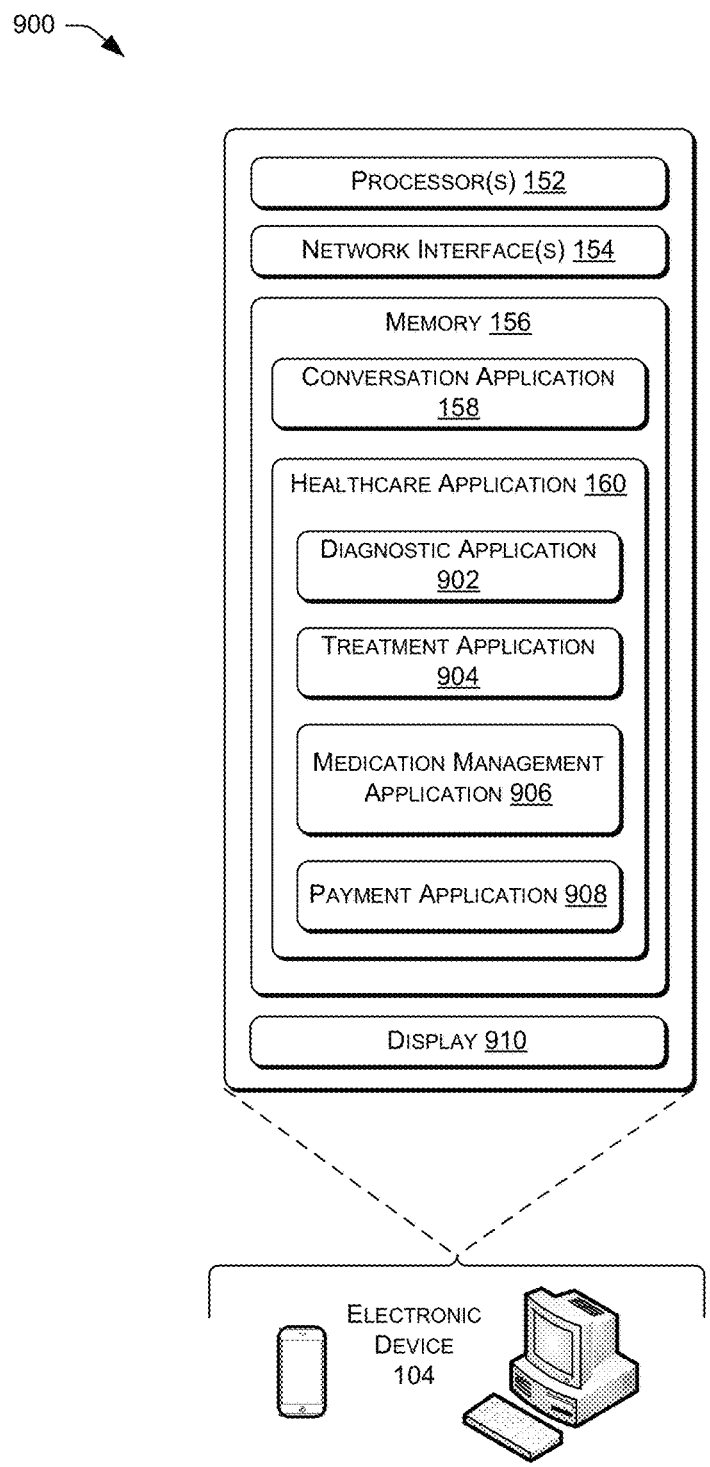
FIG. 9 illustrates example components that the electronic device of FIG. 1 may utilize when presenting a conversation GUI.

FIG. 9 illustrates example components that the electronic device 104 may utilize when assisting the patient with his or her healthcare. As illustrated, the electronic device 104 may include one or more processors 152, one or more network interfaces 154, and memory 156.

The memory 148 may store or otherwise have access to the conversation application 158 and the healthcare application 160. The healthcare application 160 may include a diagnostic application 902, a treatment application 904, a medication management application 906, and a payment application 908. The conversation application 158 may facilitate a conversation with the patient by providing a conversation graphical user interface (GUI) which is displayed on a display 910 of the electronic device 104. As discussed previously, the conversation GUI may include an entry portion to receive, from the patient, an input in a form of speech or text, and an area to visually convey the conversation. The area that visually conveys the conversation may present user dialog representations associated with the input from the patient and device dialog representations associated with responses from the virtual assistant.

The diagnostic application 902 facilitates diagnosing a medical condition of the patient. The diagnostic application 902 may access data stores that describe various diseases and associated symptoms as well as access medical records of the patient. The diagnosis determined by the diagnostic application 902 may be presented as a response in the conversation GUI. The diagnosis presented by the diagnostic application 902 may be based on real-time communication between the electronic device 104 and a medical professional. Thus, in some implementations the electronic device 104 may use analytical algorithms and data stores to arrive at an automated diagnosis of the patient, but in other implementations the electronic device 104 may convey information (e.g., symptoms) collected from the patient to a medical professional who is available to review and respond.

The treatment application 904 facilitates the patient obtaining treatment for his or her medical conditions. The treatment application 904 may assist the patient in self treating by using a disease management algorithm to identify steps that the patient can take in order to mitigate or treat the disease or disease symptoms. For treatment that requires something more than self-care, the treatment application 904 can assist the patient in obtaining treatment from medical professionals by assisting the patient in making appointments with medical professionals.

The medication management application 906 facilitates the patient obtaining and using medication. When the patient has received a new prescription from a medical professional or when it is time to refill an existing prescription, the medication management application 906 may submit a request to a pharmacy on behalf of the patient. The request may be submitted automatically, for example every 30 days or after a new prescription is received from a medical professional. Additionally, the medication management application 906 may provide reminder or alarm services that remind the patient when to take medication and may additionally instruct the patient as to the proper way of taking the medication (e.g., with food, on empty stomach, etc.).

The payment application 908, can assist with all aspects of payment and insurance related to healthcare. In some implementations, the payment application 908 may facilitate the submission of insurance claims for payment of healthcare expenses. Additionally, the payment application 908 may provide the patient with an estimate of insurance coverage for a procedure or other medical service. When it is time to make a payment, either for services covered by insurance or not, the payment application 908 may facilitate the payment by processing authorization from the patient to access funds in an account and make a payment to a healthcare entity. Thus, the patient may complete transactions with healthcare entities from within the healthcare application 160 without separately accessing a mobile payment system, a credit card, etc.

While FIG. 9 illustrates the described components as residing on the electronic device 104, in other instances some or all of these components may reside in another location. For instance, these components may reside in whole or part on each of the virtual-assistant service 116, the healthcare entity 106, the electronic device 104, or at any other location.

Figure 10:
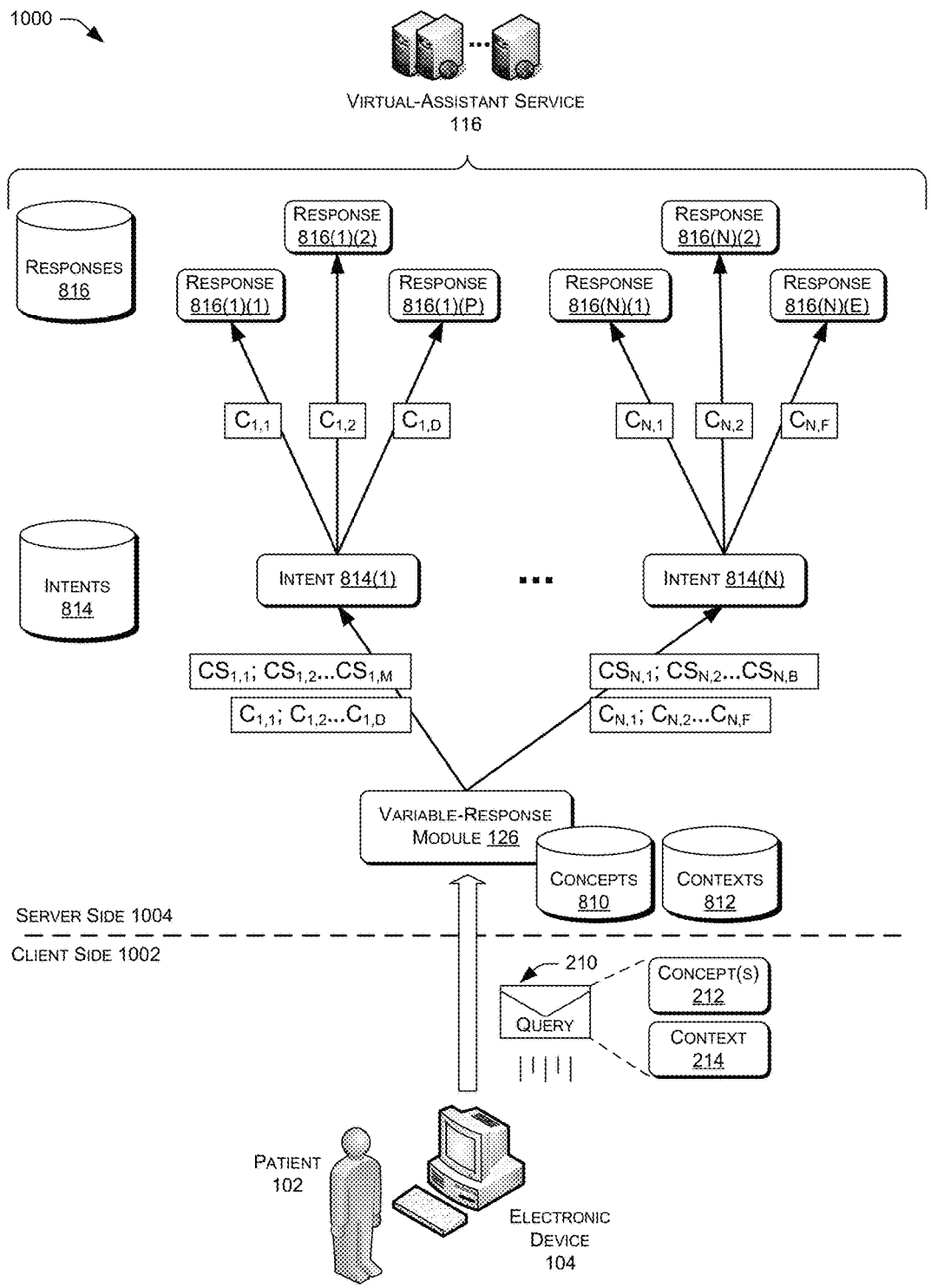
FIG. 10 illustrates how the virtual-assistant service may determine a response to provide to a patient in response to receiving the input. As illustrated, the service may first map the input to a particular intent with reference to both concepts expressed in the input and a context associated with the input. After mapping the input to an intent, the service may then map the intent to an appropriate response with reference to the context of the input.

FIG. 10 shows an example illustration 1000 how the virtual-assistant service 116 may determine a response to provide to the example patient 102 upon receiving a query 210 from the patient 102 via the conversation GUI 114. In this example, the query 210 is provided from the patient 102 on a lower or client side 1002 of the illustration 1000, while the determining of a response to provide to the query 210 is illustrated as being performed on a top or server side 1004 of the illustration 1000. Of course, in other implementations, different portions of the operations may be performed at other locations.

As FIG. 10 depicts, the example query again includes strings of words or phrases from which one or more concepts 212 can be derived, and one or more pieces of context 214. Upon receiving the query 210, the variable-response module 126 may identify, potentially with reference to the datastores 810 and 812, the concepts 212 and context 214 of the query 210. Based on the identified set of concepts 212 of the query 210 (or "concept set") and the identified pieces of context 214 of the query 210 (or "context"), the variable-response module 126 may map the query 210 to one of multiple different intents 814(1), . . . , 814(N). For instance, FIG. 10 illustrates that a query 210 having a concept set "$CS_{1,1}$" and a context "$C_{1,1}$" maps to the intent 814(1), while a query 210 having a concept set "$CS_{N,1}$" and a context "$C_{N,1}$" maps to the intent 814(N). In some instances, a concept set 212 may map to more than one intent 814 and, therefore, the context 214 of the query 210 may be used to determine which intent 814 to map the query 210 to. That is, in instances where a concept set 212 of a query 210 maps to multiple different intents 814, the intents 814 may compete for the query 210 based on the context 214 of the query 210. As used herein, a letter (e.g., "N", "E", etc.) represents any integer that is greater than zero.

The learning module 818 may provide input for use in mapping the concepts 212 and context 214 to different intents 814. For instance, the learning module 818 may over time learn diction or expressions of a patient (e.g., when the patient says "pills," she means "prescription medication"). The learning module 818 may also learn behavior or patterns or other characteristics that may impact the mapping to intents. For instance, if the patient typically requests posting of cholesterol information to her health-related social networking site but does not share her weight on the social networking site, the phrase "upload the health information" from the patient after she has accessed data about her cholesterol might map to action to post her cholesterol score on the social networking site, whereas this same phase following measurement of the patient's weight may be interpreted as a desire to transfer locally stored weight data from the electronic device to the patient's on-line medical records. Accordingly, context, concepts, and learned characteristics may all play a roll, together or individually, in mapping input to intents.

After mapping the query 210 to an intent 814, the variable-response module 126 may then map the intent 814 to an appropriate response 816(1)(1), . . . , 816(N)(E) with reference to the context 214 of the query 210. For instance, for a query 210 that the module 126 has mapped to the intent 814(1) and that has a context "$C_{1,1}$", the module 126 maps this query 210 to a response 816(1)(1). In some instances, of course, a response may be common (or utilized) across multiple different intents 814. After determining the response 816 based on the context 214, the virtual-assistant service 116 may then provide this response 816 to the patient 102, such as directly to the electronic device 104 or to the healthcare entity 106 for providing to the electronic device 104 (and/or to another device associated with the patient).

Throughout the process, the responses 816 are thus based on assumptions surrounding correct recognition of the input, derivation of concepts 212, understanding context 214, mapping to intents 814, and mapping to responses 816. Several responses 816 may be generated by the variable-response module 126. From these responses, the variable-response module 126 evaluates which is the most appropriate. This may be based on a cumulative confidence value or some other mechanism.

Example Processes

Figure 11A:
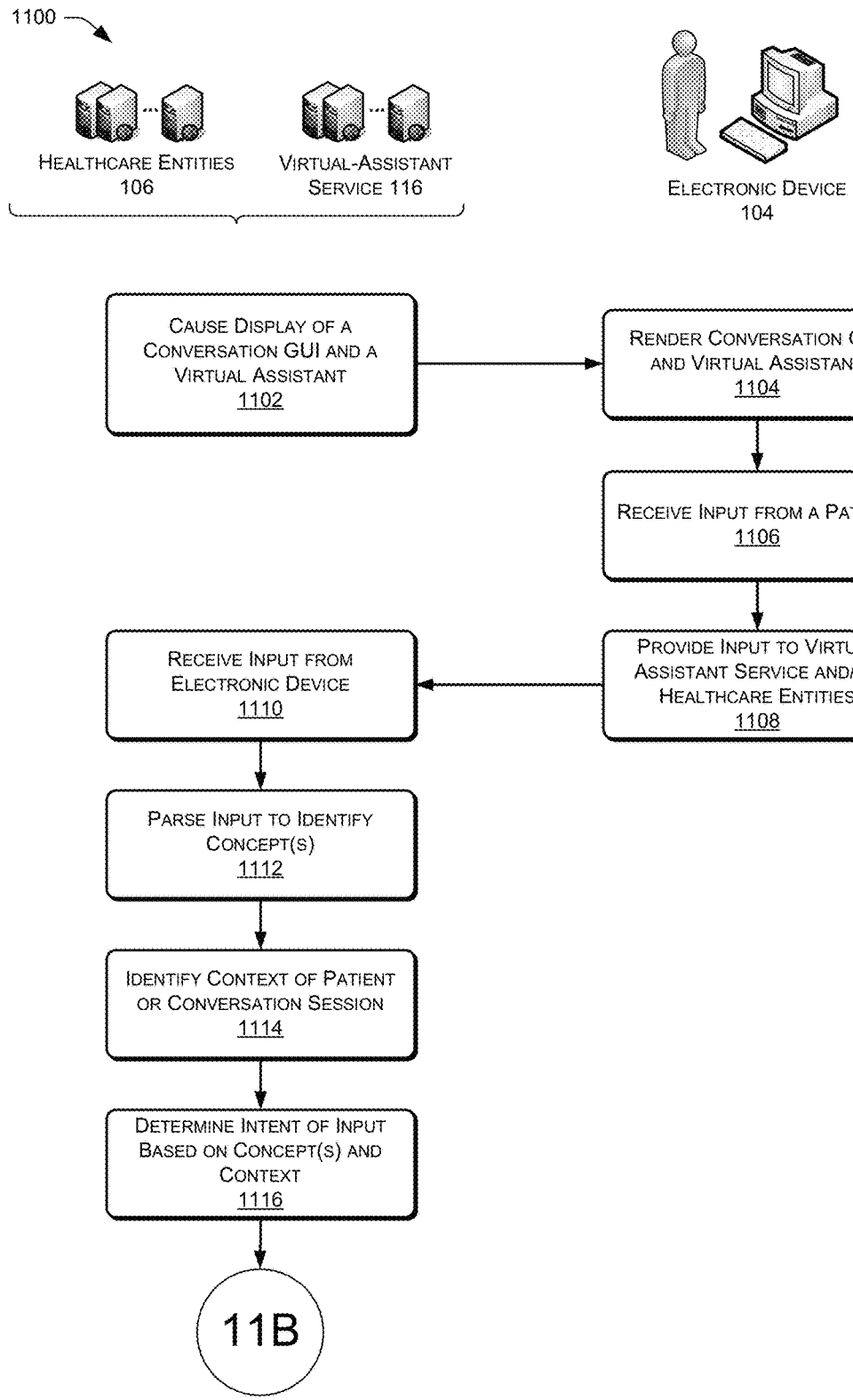
FIGS. 11A-B collectively illustrate an example process that includes the example patient providing a query via the conversation GUI and the service provider and/or the virtual-assistant service determining a response to provide to the patient.
Figure 11B:
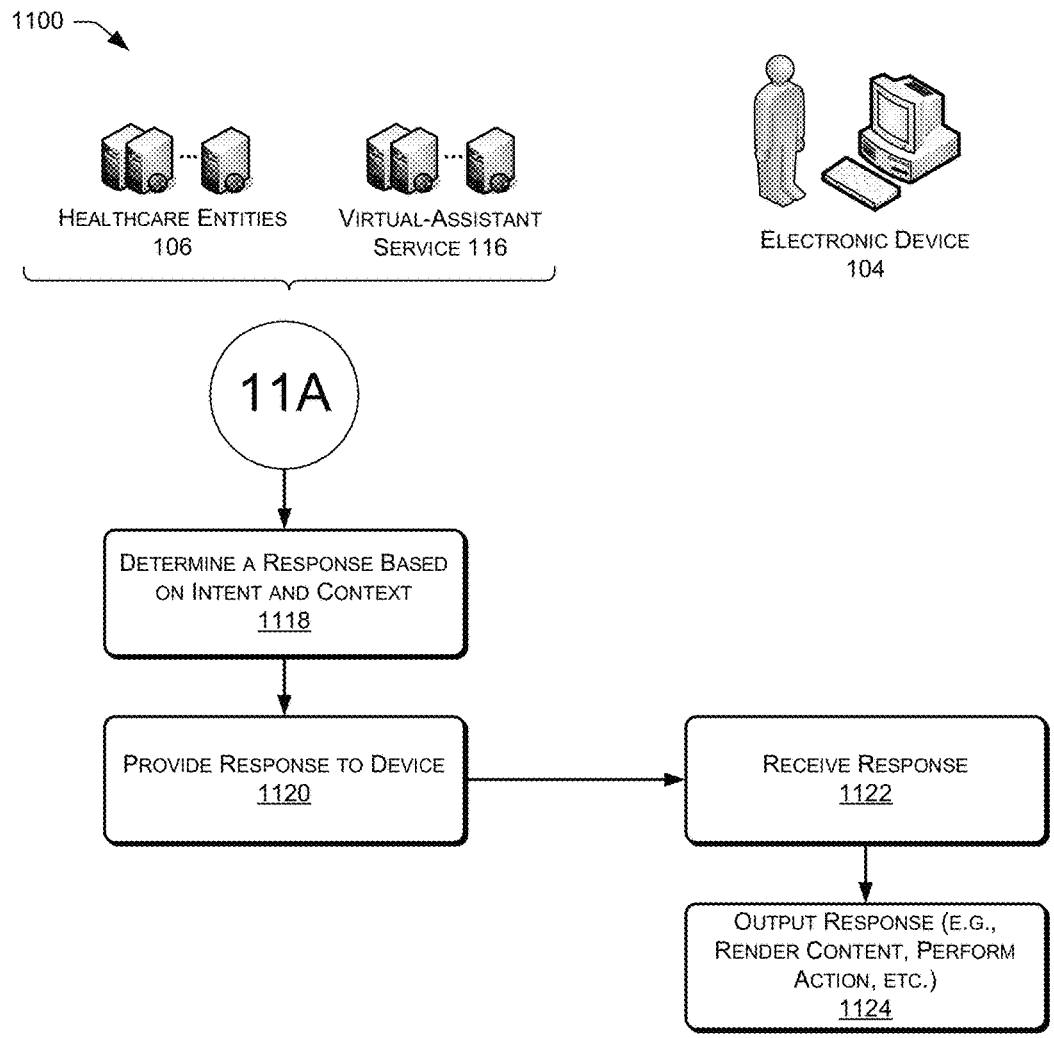

FIGS. 11A-B collectively illustrate an example process 1100 that includes the example patient 102 providing a query via the conversation GUI 114 and the healthcare entity 106 and/or the virtual-assistant service 116 determining a response to provide to the patient 102. Consistent with the discussion above, this response may take a context of the query into account both when identifying an intent of the query and when identifying an appropriate response. In this example, operations illustrated beneath the electronic device 104 may be performed by this electronic device 104 in some examples, while operations illustrated beneath the healthcare entities 106 and the virtual-assistant service 116 may be performed by the entities and/or the service in some examples. However, it is to be appreciated that in other implementations the operations may be performed at any other location(s).

The process 1100 is illustrated as a logical flow graph, each operation of which represents a sequence of operations that can be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the process.

At 1102, the healthcare entities 106 and/or the virtual-assistant service 116 causes display of the conversation GUI including a virtual assistant on the electronic device 104. The conversation GUI may be the sole graphics on a screen, or it may on or adjacent to content from a healthcare entity.

At 1104, and in response, the electronic device 104 renders the conversation GUI which may be similar to the conversation GUI 114 discussed above. At 1106, the electronic device 104 receives input from the patient interacting with the conversation GUI. The input may comprise a string of text, verbal input, or some other input (e.g., gesture, video images, etc.). At 1108, the electronic device 104 provides the input to the healthcare entities 106 and/or the virtual-assistant service 116, which receives the input at 1110.

At 1112, the healthcare entities 106 and/or the virtual-assistant service 116 parse the input to identify one or more concepts expressed therein. That is, the healthcare entities 106 and/or the virtual-assistant service 116 may use natural language processing techniques to identify concepts specified by the patient in the input received at 1106. These concepts may be determined with reference to contents of the patient's query in any suitable manner. In some examples, the concept(s) of a query are determined at least partly with reference to one or more keywords expressed within the input. For instance, the concepts may be determined using relatively basic keyword matching in some instances. This matching can be improved with the learning module 818, so that specific words or phrases can be mapped to a given concept based on learned specific user behavior. In other instances, meanwhile, the concepts may be determined using a much richer process as described below.

In these instances, when the healthcare entities 106 and/or the virtual-assistant service 116 receives the input in the form of a string of text, the healthcare entities 106 and/or the virtual-assistant service 116 preprocesses the string by, for example, identifying one or more tokens within the string. The tokens may comprise words, phrases, symbols, or the like that signify some sort of meaning within the query. After tokenizing the string of text, the healthcare entities 106 and/or the virtual-assistant service 116 may then map each of these tokens and/or ordered patterns of the tokens to a more general set, known as a "vocab item." A vocabulary item may comprise a general set of multiple different tokens having a meaning that is common amongst these tokens. For instance, the tokens "prescription," "pills," and "drugs" may each map to a vocabulary item representing "prescription medication." User specific learning via the learning module 818 can produce tokens like "pills," where the patient always uses this word to mean "prescription medication."

After mapping tokens and/or patterns of tokens from the original string of text to one or more vocab items, the healthcare entities 106 and/or the virtual-assistant service 116 may then pattern match the vocab items to one or more concepts. That is, each concept may be associated with multiple different vocab-item patterns (e.g., "(vocab item A, vocab item D, vocab item F)", "(vocab item B, vocab item E)", "(vocab item X)", etc.). In addition, some of these patterns may be associated with a context. For instance, the pattern "(vocab item B, vocab item E)" may map to a particular concept given a particular context (e.g., the patient is admitted to a hospital), but not otherwise. By pattern matching the vocab items to the concepts, the healthcare entities 106 and/or the virtual-assistant service 116 may identify one or more concepts that are associated with the input received from the patient. Key phrases can also be learned or matched to a concept. For example, a patient may use the phrase "what's the cost" which the learning module 818 learns that the patient means identify the member co-pay for the medical service that was most recently discussed in the dialog, so the system maps this phrase to the concept of query the patient's insurance provider for an estimated member charge.

In addition or in the alternative to the techniques described above, the healthcare entities 106 and/or the virtual-assistant service 116 may identify concept(s) of a query with reference to a graph data structure that maintains correlations between words. The graph data structure, for instance, may maintain a hierarchy of words (e.g., hypernyms and hyponyms). The techniques may utilize this hierarchy to identify one or more concepts within a string of text. For instance, if a string contains the word "CAT scan," the techniques may analyze the graph data structure to determine that "CAT scan" is a type of a "medical image" which is a type of "health record." The techniques may then identify "medical image" and/or "health record" as a concept within the input. Of course, in this and other processes used to determine concepts within inputs, the techniques may reference other factors associated with the inputs, such as the ordering of words, parts of speech of words, and the like. Furthermore, while a few different example techniques for identifying concepts have been described, it is to be appreciated that other new and/or known techniques may be used to identify concepts within an input.

At 1114, the healthcare entities 106 and/or the virtual-assistant service 116 may also identify a context associated with the patient or with a session of the patient on the platform of the healthcare entities 106. The context may include medical records of the patient, prescription medication for the patient, healthcare providers for the patient, readings of medical devices used by the patient, insurance records of the patient, or the like. At 1116, the healthcare entities 106 and/or the virtual-assistant service 116 determine an intent of the input based on the identified concept(s) from 1112 and the identified context from 1114.

FIG. 11B continues the illustration of the process 1100 and includes, at 1118, the healthcare entities 106 and/or the virtual-assistant service 116 determining a response to provide to the input based on the intent and the identified context. In some instances, the portion of the context referenced in mapping the input to the intent represents the same portion of context referenced in mapping the intent to the response. In other instances, meanwhile, the healthcare entities 106 and/or the virtual-assistant service 116 map the query to an intent using a first portion of context, while using a second, different portion of the context when mapping the intent to the response. Of course, in still other instances, these portions of content may include at least one common piece of context and at least one piece of context that is not commonly used.

At 1120, the healthcare entities 106 and/or the virtual-assistant service 116 provides the response to the electronic device 104 of the patient or to another electronic device associated with the patient to be rendered as a communication from the virtual assistant. Thus, an avatar representing the virtual assistant may present the response to the patient. In this example, the electronic device 104 receives the response at 1122 and, at 1124, outputs the response to the patient as part of the conversation GUI. For instance, the electronic device 104 may render text, one or more links, audible content, and the like as a response from the virtual assistant, and the electronic device 104 may also perform one or more actions specified in the response.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. One or more non-transitory computer-readable media storing computer-executable instructions that, when executed by one or more processors, cause the one or more processors to perform acts comprising:
   causing display of a conversation user interface along with a visual representation of a virtual assistant, the virtual assistant being configured with a persona;
   learning one or more characteristics about a medical-related user from a conversation with the medical-related user via the conversation user interface;
   receiving user input of the medical-related user during a later conversation, the user input comprising at least one of verbal input, keypad input, or touch input;
   parsing the user input to identify one or more concepts expressed therein;
   determining an intent of the medical-related user based at least in part on the one or more concepts;
   determining a response to the user input based at least in part on (i) a medical history for the medical-related user, (ii) the intent of the medical-related user, (iii) the one or more learned characteristics about the medical-related user, (iv) a disease management algorithm indicating information to mitigate or treat a disease or symptom, and (v) assumptions used to interpret the user input or previous user input; and
   representing the response in the conversation user interface as a message from the virtual assistant, the response including content to assist the medical-related user in managing a medical condition of the medical-related user.

2. The one or more non-transitory computer-readable media as recited in claim 1, wherein the user input is verbal input, and the verbal input is represented in the conversation user interface in a text format through a speech recognition engine.

3. The one or more non-transitory computer-readable media as recited in claim 1, wherein:
  the user input is verbal input; and
  the acts further comprise authenticating an identity of the medical-related user through analysis of voice patterns contained in the verbal input.

4. The one or more non-transitory computer-readable media as recited in claim 1, wherein the response to the user input is determined based at least in part on past behavior of the medical-related user.

5. The one or more non-transitory computer-readable media as recited in claim 1, wherein the response to the user input is determined based at least in part on a status of the medical-related user as checked in or checked out of a healthcare facility.

6. The one or more non-transitory computer-readable media as recited in claim 1, wherein the response to the user input is determined based on at least one of medical research results, nutrition information, or insurance information.

7. The one or more non-transitory computer-readable media as recited in claim 1, wherein the response to the user input is determined based on at least one of:
  whether or not the medical-related user has checked in with a healthcare entity;
  a status of a medical device used by the medical-related user;
  a level of insurance coverage available to the medical-related user;
  a prescription medication used by the medical-related user;
  a diagnosed condition of the medical-related user;
  a time of day at which the medical-related user provides the user input to the virtual assistant;
  a date on which the medical-related user provides the user input to the virtual assistant;
  an age of the medical-related user;
  a location of the medical-related user; or
  a device type from which the medical-related user provides the user input.

8. The one or more non-transitory computer-readable media as recited in claim 1, wherein the acts further comprise causing an action to be performed on behalf of the medical-related user, the action comprising at least one of:
  scheduling a medical appointment on behalf of the medical-related user;
  initiating a prescription refill request on behalf of the medical-related user;
  accessing data from a medical device on behalf of the medical-related user;
  communicating with an insurance provider on behalf of the medical-related user; or
  altering a previously initiated action on behalf of the medical-related user.

9. A portable computing device comprising:
  the one or more non-transitory computer-readable media as recited in claim 1; and
  the one or more processors to execute the computer-executable instructions stored on the one or more non-transitory computer-readable media to perform the acts.

10. A computing system comprising:
  one or more servers for hosting content;
  the one or more non-transitory computer-readable media as recited in claim 1; and
  the one or more processors to execute the computer-executable instructions stored on the one or more non-transitory computer-readable media to perform the acts.

11. The one or more non-transitory computer-readable media as recited in claim 1, wherein each of the one or more characteristics includes at least one of a health status of the medical-related user or a treatment regimen of the medical-related user.

12. The one or more non-transitory computer-readable media as recited in claim 1, wherein the acts further comprise:
  determining that a voice of the user is modified by a health condition; and
  correcting a word or a phase in the user based at least in part on determining that the voice of the user is modified by the health condition.

13. A method comprising:
  initiating, by one or more processors, a conversation with a user by causing information representing a virtual assistant to be displayed via a mobile device, the virtual assistant being configured with a persona;
  learning one or more characteristics about the user from the conversation with the user;
  receiving, by the one or more processors, a medical query during the conversation with the virtual assistant, the medical query comprising at least one of verbal input, keypad input, or touch input;
  performing natural language processing with the medical query to identify one or more concepts of the medical query;
  determining, by the one or more processors, a response to the medical query based at least in part on (i) a medical history for the user, (ii) an intent of the user, (iii) the one or more learned characteristics, (iv) the one or more concepts of the medical query, and (v) medical information, the medical information comprising at least one of:
    a treatment regimen;
    health insurance eligibility;
    a medical diagnostic algorithm;
    nutrition information;
    prescription medication for the user;
    a healthcare entity for the user;
    a reading of a medical device; or
    an insurance record of the user; and
  providing, by the one or more processors, the response for output via the mobile device as a message from the virtual assistant.

14. The method as recited in claim 13, wherein the response from the virtual assistant is provided as audio output.

15. The method as recited in claim 13, wherein the medical query relates to a medical condition of the user.

16. The method as recited in claim 13, wherein the response includes information about a comparison between a metric of the user and a metric for another user.

17. The method as recited in claim 16, wherein the metric of the user is obtained from at least one of an electronic medical record of the user, input provided by the user, a result of a test administered to the user, or data from the medical device.

18. A computing device comprising:
  one or more computer-readable media storing computer-executable instructions; and the one or more processors to execute the computer-executable instructions stored on the one or more computer-readable media to perform the method of claim 13.

19. A system comprising:

one or more processors; and memory storing computer-executable instructions that, when executed by the one or more processors, cause the one or more processors to perform operations comprising:

- initiating a conversation with a user by causing information representing a virtual assistant to be displayed via a mobile device, the virtual assistant being configured with a persona;
- learning one or more characteristics about the user from the conversation with the user;
- receiving a medical query during the conversation with the virtual assistant, the medical query comprising at least one of verbal input, keypad input, or touch input;

performing natural language processing with the medical query to identify one or more concepts of the medical query;

- determining a response to the medical query based at least in part on (i) a medical history for the user, (ii) an intent of the user, (iii) the one or more learned characteristics, (iv) the one or more concepts of the medical query, and (v) medical information, the medical information comprising at least one of:
- a treatment regimen;
- health insurance eligibility;
- a medical diagnostic algorithm;
- nutrition information;
- prescription medication for the user;
- a healthcare entity for the user;
- a reading of a medical device; or
- an insurance record of the user; and
- providing the response for output via the mobile device as a message from the virtual assistant.

20. The system as recited in claim 19, wherein the response from the virtual assistant is provided as audio output.

21. The system as recited in claim 19, wherein the medical query relates to a medical condition of the user.

22. The system as recited in claim 19, wherein the response includes information about a comparison between a metric of the user and a metric for another user.

23. The system as recited in claim 22, wherein the metric of the user is obtained from at least one of an electronic medical record of the user, input provided by the user, a result of a test administered to the user, or data from the medical device.

24. The system as recited in claim 19, wherein the response is determined based on at least one of:

- whether or not the user has checked in with the healthcare entity;
- a status of the medical device;
- a level of insurance coverage available to the user; or
- a diagnosed condition of the user.

25. The system as recited in claim 19, wherein the response is determined based on at least one of:

- a time of day at which the user provides the medical query;
- a date on which the user provides the medical query;
- an age of the user;
- a location of the user; or
- a device type from which the user provides the medical query.

* * * * *